United States Patent
Gazit et al.

(10) Patent No.: US 10,638,948 B2
(45) Date of Patent: May 5, 2020

(54) IMAGING BIOMARKERS FOR THE DIAGNOSIS AND PROGNOSIS OF BACK PAIN AND RELATED CONDITIONS

(71) Applicant: Cedars-Sinai Medical Center, Los Angeles, CA (US)

(72) Inventors: Dan Gazit, Los Angeles, CA (US); Debiao Li, Pasadena, CA (US); Hyun Bae, Los Angeles, CA (US); Gadi Pelled, Los Angeles, CA (US); Zulma Gazit, Los Angeles, CA (US); Qi Liu, Beverly Hills, CA (US); Wafa Tawackoli, Beverly Hills, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 1130 days.

(21) Appl. No.: 14/785,235

(22) PCT Filed: Apr. 18, 2014

(86) PCT No.: PCT/US2014/034720
§ 371 (c)(1),
(2) Date: Oct. 16, 2015

(87) PCT Pub. No.: WO2014/172682
PCT Pub. Date: Oct. 23, 2014

(65) Prior Publication Data
US 2016/0081578 A1 Mar. 24, 2016

Related U.S. Application Data

(60) Provisional application No. 61/813,996, filed on Apr. 19, 2013.

(51) Int. Cl.
*A61B 5/055* (2006.01)
*A61B 5/145* (2006.01)
*A61B 5/00* (2006.01)

(52) U.S. Cl.
CPC .............. *A61B 5/055* (2013.01); *A61B 5/004* (2013.01); *A61B 5/14532* (2013.01);
(Continued)

(58) Field of Classification Search
CPC ....... A61B 5/055; A61B 5/7282; A61B 5/004; A61B 5/14546; A61B 5/4824;
(Continued)

(56) References Cited

U.S. PATENT DOCUMENTS

2011/0054299 A1 3/2011 Ling et al.
2011/0087087 A1 4/2011 Peacock, III et al.
(Continued)

FOREIGN PATENT DOCUMENTS

EP 2986210 A1 2/2016
WO 2014172682 A1 10/2014
WO 2017214439 A1 12/2017

OTHER PUBLICATIONS

Andersen et al., Variation in the COMT gene: implications for pain perception and pain treatment. Pharmacogenomics, 2009, vol. 10, 669-684.
(Continued)

*Primary Examiner* — Peter Luong
(74) *Attorney, Agent, or Firm* — Erik Birkeneder; Nixon Peabody LLP

(57) ABSTRACT

The present invention teaches novel methods of diagnosing and prognosing conditions associated with tissue degeneration and/or pain, including intervertebral disc degeneration, discogenic pain, osteoarthritis, rheumatoid arthritis, and articular cartilage injury. Using the inventive noninvasive imaging methods, the diagnosis and prognosis of back pain and related conditions can be quickly and accurately determined by detecting one or more biomarkers disclosed herein.

27 Claims, 13 Drawing Sheets

(52) U.S. Cl.
CPC ...... *A61B 5/14539* (2013.01); *A61B 5/14546*
(2013.01); *A61B 5/4566* (2013.01); *A61B*
*5/4824* (2013.01); *A61B 5/7282* (2013.01);
*A61B 5/407* (2013.01)

(58) Field of Classification Search
CPC ............ A61B 5/14539; A61B 5/14532; A61B
5/4566; A61B 5/407
See application file for complete search history.

(56) References Cited

U.S. PATENT DOCUMENTS

| | | | |
|---|---|---|---|
| 2014/0316246 A1* | 10/2014 | Gounis | A61B 5/0263 600/410 |
| 2015/0323632 A1 | 11/2015 | Sun | |
| 2016/0082132 A1* | 3/2016 | Yang | A61K 49/10 424/9.3 |
| 2016/0136310 A1 | 5/2016 | Bradford et al. | |

OTHER PUBLICATIONS

Andersson, G. B., Epidemiological features of chronic low-back pain. Lancet, 1999, vol. 354, pp. 581-585.
Asicioglu et al., Maternal and perinatal outcomes of eclampsia with and without HELLP syndrome in a teaching hospital in western Turkey, J. Obstet. Gynaecol., 2014, vol. 34, pp. 326-331.
Auerbach et al., In vivo quantification of human lumbar disc degeneration using T(1rho)-weighted magnetic resonance imaging, Eur. Spine J., 2006, vol. 15, Suppl. 3, pp. S338-S344.
Boos et al., Tissue characterization of symptomatic and asymptomatic disc herniations by quantitative magnetic resonance imaging, J. Orthop. Res., 1997, vol. 15, pp. 141-149.
Borthakur et al., T1rho magnetic resonance imaging and discography pressure as novel biomarkers for disc degeneration and low back pain, Spine (Phila Pa 1976), 2011, vol. 36, pp. 2190-2196.
Chatani et al., Topographic differences of 1H-NMR relaxation times (T1, T2) in the normal intervertebral disc and its relationship to water content, Spine (Phila Pa 1976), 1993, vol. 18, pp. 2271-2275.
Chiu et al., Magnetic resonance imaging measurement of relaxation and water diffusion in the human lumbar intervertebral disc under compression in vitro, Spine (Phila Pa 1976), 2001, vol. 26, pp. E437-E444.
Coppes et al., Innervation of annulus fibrosis in low back pain, Lancet, 1990, vol. 336, pp. 189-190.
Cuesta et al., Acid-sensing ion channels in healthy and degenerated human intervertebral disc, Connect Tissue Res., 2014, vol. 55, pp. 197-204.
Donnerer et al., Increased content and transport of substance P and calcitonin gene-related peptide in sensory nerves innervating inflamed tissue: evidence for a regulatory function of nerve growth factor in vivo. Neuroscience, 1992, vol. 49, pp. 693-698.
Dray et al., Bradykinin and inflammatory pain. Trends Neurosci., 1993, vol. 16, pp. 99-104.
Freemont et al., Nerve ingrowth into diseased intervertebral disc in chronic back pain, Lancet, 1997, vol. 350, pp. 178-181.
Gilbert et al., Acidic pH promotes intervertebral disc degeneration: Acid-sensing ion channel-3 as a potential therapeutic target, Sci. Rep., 2016, vol. 6, 37360, pp. 1-12.
Gruber et al., Genome-wide analysis of pain-, nerve- and neurotrophin—related gene expression in the degenerating human annulus. Mol. Pain, 2012, vol. 8 (63), pp. 1-18.
Haris et al., Exchange rates of creatine kinase metabolites: feasibility of imaging creatine by chemical exchange saturation transfer MRI. NMR Biomed., 2012, vol. 25, pp. 1305-1309.
Ichimura et al., Cell culture of the intervertebral disc of rats: factors influencing culture, proteoglycan, collagen, and deoxyribonucleic acid synthesis, J. Spinal Disord. 1991, vol. 4, pp. 428-436.

Kang et al., Can magnetic resonance imaging accurately predict concordant pain provocation during provocative disc injection? Skeletal Radiol., 2009, vol. 38, pp. 877-885.
Kim et al., Assessment of Glycosaminoglycan Distribution in Human Lumbar Intervertebral Discs Using Chemical Exchange Saturation Transfer at 3 T: Feasibility and Initial Experience, NMR Biomed, 2011, vol. 24(9), pp. 1137-1144.
Kim et al., A review of optimization and quantification techniques for chemical exchange saturation transfer MRI toward sensitive in vivo imaging, Contrast Media Mol. Imaging, 2015, vol. 10, pp. 163-178.
Lefevre-Colau et al., Frequency and interrelations of risk factors for chronic low back pain in a primary care setting, PLoS One, 2009, vol. 4, e4874, pp. 1-7.
Liu et al., Biological behavior of human nucleus pulposus mesenchymal stem cells in response to changes in the acidic environment during intervertebral disc degeneration, Stem Cells Dev., 2017, vol. 26(12), pp. 901-911.
Majumdar et al., Diagnostic tools and imaging methods in intervertebral disk degeneration. Orthop Clin North Am., 2011, vol. 42, pp. 501-511.
Menkin, V., Biochemical Mechanisms in Inflammation, Br. Med. J., 1960, vol. 1, pp. 1521-1528.
Mizrahi et al., Nucleus pulposus degeneration alters properties of resident progenitor cells, Spine, 2013, J12, pp. 803-814.
Navone et al., Expression of neural and neurotrophic markers in nucleus pulposus cells isolated from degenerated intervertebral disc, J. Orthop. Res., 2012, vol. 30, 1470-1477.
Ohtori et al., Up-regulation of acid-sensing ion channel 3 in dorsal root ganglion neurons following application of nucleus pulposus on nerve root in rats, Spine (Phila Pa 1976), 2006, vol. 31, pp. 2048-2052.
Orita et al., Inhibiting nerve growth factor or its receptors downregulates calcitonin gene-related peptide expression in rat lumbar dorsal root ganglia innervating injured intervertebral discs. J. Orthop. Res., 2010, vol. 28, pp. 1614-1620.
Peng et al., The pathogenesis of discogenic low back pain, J. Bone Joint Surg. Br., 2005, vol. 87, pp. 62-67.
Purmessur et al., Expression and regulation of neurotrophins in the nondegenerate and degenerate human intervertebral disc, Arthritis Res. Ther., 2008, vol. 10, R99, p. 1-9.
Raj, P. P., Intervertebral disc: anatomy-physiology-pathophysiology-treatment, Pain Pract., 2008, vol. 8, pp. 18-44.
Richardson et al., Degenerate human nucleus pulposus cells promote neurite outgrowth in neural cells, PLoS One 7, 2012, e47735, pp. 1-8.
Sheyn et al., PTH promotes allograft integration in a calvarial bone defect, Mol. Pharm. 2013, vol. 10, pp. 4462-4471.
Sun et al., Detection of the ischemic penumbra using pH-weighted MRI, J. Cereb. Blood Flow Metab., 2007, vol. 27, pp. 1129-1136.
Sun et al., Relaxation-compensated fast multislice amide proton transfer (APT) imaging of acute ischemic stroke, Magn. Reson. Med., 2008, vol. 59, pp. 1175-1182.
Trattnig et al., Lumbar intervertebral disc abnormalities: comparison of quantitative T2 mapping with conventional MR at 3.0 T, Eur Radiol., 2010, vol. 20, pp. 2715-2722.
Uchiyama et al., Expression of acid-sensing ion channel 3 (ASIC3) in nucleus pulposus cells of the intervertebral disc is regulated by p75NTR and ERK signaling. J. Bone Miner. Res., 2007, vol. 22, pp. 1996-2006.
Urban et al., Swelling pressure of the inervertebral disc: influence of proteoglycan and collagen contents, Biorheology, 1985, vol. 22, pp. 145-157.
Urban et al., Nutrition of the intervertebral disc, Spine, 2004, vol. 29, pp. 2700-2709.
Vinogradov et al., CEST: from basic principles to applications, challenges and opportunities, J. Magn. Reson., 2013, vol. 229, pp. 155-172.
Wada et al., Glycosaminoglycan chemical exchange saturation transfer in human lumbar intervertebral discs: Effect of saturation pulse and relationship with low back pain, J. Magn. Reson. Imaging., 2017, vol. 45, pp. 863-871.

(56) References Cited

OTHER PUBLICATIONS

Watanabe et al., Relationship between immunostaining intensity and antigen content in sections, J. Histochem. Cytochem., 1996, vol. 44, pp. 1451-1458.

Zhao et al., The cell biology of intervertebral disc aging and degeneration, Ageing Res. Rev., 2007, vol. 6, pp. 247-261.

Zhou et al., Using the amide proton signals of intracellular proteins and peptides to detect pH effects in MRI, Nat. Med. 2003, vol. 9, pp. 1085-1090.

Zhou et al., Defining an Acidosis-Based Ischemic Penumbra from pH-Weighted MRI, Transl. Stroke Res., 2011, vol. 3, pp. 76-83.

Zhou et al., Quantitative chemical exchange saturation transfer MRI of intervertebral disc in a porcine model. Magn. Reson. Med., 2016, vol. 76, pp. 1677-1683.

International Search Report and Written Opinion dated Sep. 23, 2014 for International application No. PCT/US2014/034720.

Tao Jin, et al., Spin-locking vs. chemical exchange saturation transfer MRI for investigating chemical exchange process between water and labile metabolite protons, Magnetic Resonance in Medicine, May 2011, pp. 1448-1460, vol. 65(5).

M. Kim, et al., Assessment of glycosaminoglycan distribution in human lumbar intervertebral discs using chemical exchange saturation transfer, Proceedings of the International Society for Magnetic Resonance in Medicine, 2010, p. 539, vol. 18.

K. Li, et al., Chemical Exchange Saturation Transfer and R1Rho Dispersions of Polypeptides with Varying Complexities, Proceedings of the International Society for Magnetic Resonance in Medicine, 2011, p. 4495, vol. 19.

Chen, W. et al., Quantitative T(1)(rho) imaging using phase cycling for B0 and B1 field inhomogeneity composition, Magn Reson Imaging, 2011, 29:608-619.

Kim, M. et al., Water saturation shift referencing (WASSR) for chemical exchange saturation transfer (CEST) experiments, Magn. Reson. Med., 2009, 61:1441-1450.

Li, X. et al., Simultaneous acquisition of T1p and T2 quantification in knee cartilage: reproducibility and diurnal variation, Magn Reson Imaging, 2014, 39(5):1287-1293.

Melkus, G. et al., Ex vivo porcine model to measure pH dependence of chemical exchange saturation transfer effect of glycosaminoglycan in the intervertebral disc, Magn Reson Med., 2014 71(5):1743-1749.

Saar, G. et al., Assessment of glycosaminoglycan concentration changes in the intervertebral disc via CEST, NMR Biomed., 2012, 25(2):255-261.

Sun, PZ. et al., Simplified and scalable numerical solution for describing multi-pool chemical exchange saturation transfer (CEST) MRI contrast, J. Magn Reson., 2010, 205(2):235-241.

Zaiss M. et al. Quantitative separation of CEST effect from magnetization transfer and spillover effects by Lorentzian-line-fit analysis of z-spectra, J. Magn. Reson., 2011, 211:149-155.

Zu, Z. et al., Optimizing pulsed-chemical exchange saturation transfer (CEST) imaging sequences, Magn Reson Med., 2011, 66(4):1100-1108.

Zuo, J. et al., Assessment of intervertebral disc degeneration with magnetic resonance single-voxel spectroscopy, Magn. Reson Med, 2009, 62(5):1140-1146.

Zuo, J. et al., In vivo intervertebral disc characterization using magnetic resonance spectroscopy and T1(rho) imaging: association with discography and Oswestry Disability Index and SF-36, Spine (Phila Pa 1976), 2012, 37(3):214-221.

International Preliminary Report on Patentability for PCT/US2014/034720 dated Oct. 20, 2015, 8 pages.

International Search Report and Written Opinion for PCT/US2017/036617 dated Aug. 29, 2017, 12 pages.

EP 14786020.9 Extended European Search Report dated Sep. 20, 2016, 6 pages.

An et al., Introduction: Disc Degeneration: Summary, Spine, 2004, vol. 29, pp. 2677-2678.

Antoniou et al., Quantitative Magnetic Resonance Imaging in the Assessment of Degenerative Disc Disease, Magnetic Resonance in Medicine, 1998, vol. 40, pp. 900-907.

Borenstein et al., The Value of Magnetic Resonance Imaging of the Lumbar Spine to Predict Low-Back Pain in Asymptomatic Subjects: A Seven-Year Follow-Up Study, Journal of Bone and Joint Surgery, 2001, vol. 83A(9), pp. 1306-1311.

Blumenkrants et al., In Vivo 3.0-Testa Magnetic Resonance T1p and T2 Relaxation Mapping in Subjects With Intervertebral Disc Degeneration and Clinical Symptoms, Magn. Reson. Med., 2010, vol. 63(5), pp. 1193-1200.

Carragee et al., Does Discography Cause Accelerated Progression of Degeneration Changes in the Lumbar Disc: A Ten-Year Matched Cohort Study, Spine, 2009, vol. 34, pp. 2338-2345.

Dixon et al., A Concentration-Independent Method to Measure Exchange Rates in PARACEST Agents, Magnetic Resonance in Medicine, 2010, vol. 63, pp. 625-632.

Englander et al., Hydrogen Exchange, Annu. Rev. Biochem., 1972, vol. 41, pp. 903-924.

Haneder et al., Assessment of Glycosaminoglycan Content in Intervertebral Discs using Chemical Exchange Saturation Transfer at 3.0 Tesla: Preliminary Results in Patients with Low-Back Pain, Eur Radiol, 2013, vol. 23, pp. 861-868.

Heo et al., Accelerating Chemical Exchange Saturation Transfer (CEST) MRI by Combining Compressed Sensing and Sensitivity Encoding Techniques, Magnetic Resonance in Medicine, 2017, vol. 77(2), pp. 779-786.

Jin et al., Magnetic Resonance Imaging of the Amine-Proton EXchange (APEX) Dependent Contrast, Neuroimage, 2012, vol. 59(2), pp. 1218-1227.

Johannessen et al., Assessment of Human Disc Degeneration and Proteoglycan Content Using T1p-weighted Magnetic Resonance Imaging, Spine, 2006, vol. 31(11), pp. 1253-1257.

Keshari et al., Lactic Acid and Proteoglycans as Metabolic Markers for Discogenic Back Pain, Spine, 2008, vol. 33, pp. 312-317.

Kim et al., Disc Degeneration in the Rabbit: A Biochemical and Radiological Comparison Between Four Disc Injury Models, Spine, 2004, vol. 30, pp. 33-37.

Knox et al., The Incidence of Low Back Pain in Active Duty United States Military Service Members, Spine, 2011, vol. 36, pp. 1492-1500.

Lee et al., In Vitro Study of Endogenous CEST Agents at 3 T and 7 T, Contrast Media Mol Imaging, 2016,vol. 11, pp. 4-14.

Liang et al., The Relationship Between Low pH in Intervertebral Discs and Low Back Pain: A Systematic Review, Arch Med Sci, 2012, vol. 8, pp. 952-956.

Liang et al., New Hypothesis of Chronic Back Pain: Low pH Promotes Nerve Ingrowth into Damaged Intervertebral Disks, Acta Anaesthesiol Scand, 2013, vol. 57, pp. 271-277.

Ling et al., Assessment of Glycosaminoglycan Concentration In Vivo by Chemical Exchange-Dependent Saturation Transfer (gagCEST), PNAS, 2008, vol. 105, pp. 2266-2270.

Liu et al., Chemical Exchange and In Vivo Intervertebral Disc R1-RHO Dispersion Imaging: A Feasibility Study, ISMRM 21st Annual Meeting and Exhibition, 2013, vol. 3, p. 2403.

Liu et al., Reliable Chemical Exchange Saturation Transfer Imaging of Human Lumbar Intervertebral Discs Using Reduced-Field-of-View Turbo Spin Echo at 3.0 T, NMR in Biomedicine, 2013, vol. 26, pp. 1672-1679.

Liu et al., Detection of Low Back Pain using pH Level-Dependent Imaging of the Intervertebral Disc using the Ratio of R1p Dispersion and -OH Chemical Exchange Saturation Transfer (RROC), Magnetic Resonance in Medicine, 2015, vol. 73, pp. 1196-1205.

Meissner et al., Quantitative pulsed CEST-MRI using Ω-plots, NMR in Biomedicine, 2015, vol. 28, pp. 1196-1208.

Müller-Lutz et al., Gender, BMI and T2 Dependencies of Glycosaminoglycan Chemical Exchange Saturation Transfer in Intervertebral Discs, Magn Reson Imaging, 2016, vol. 34, pp. 271-275.

Nachemson et al., Intradiscal Measurements of pH in Patients with Lumbar Rhizopathies, Acta Orthopaedica Scandinavica, 1969, vol. 40, pp. 23-42.

(56) References Cited

OTHER PUBLICATIONS

Osti et al., MRI and Discography of Annular Tears and Intervertebral Disc Degeneration, Journal of Bone and Joint Surgery, 1992, vol. 74B(3), pp. 431-435.

Recuerda et al., Assessment of Mechanical Properties of Isolated Bovine Intervertebral Discs from Multi-Parametric Magnetic Resonance Imaging, BMC Musculoskeletal Disorders, 2012, vol. 13, 14 pages.

Schleich et al., Glycosaminoglycan Chemical Exchange Saturation Transfer of Lumbar Intervertebral Discs in Patients with Spondyloarthritis, Journal of Magnetic Resonance Imaging, 2015, vol. 42, pp. 1057-1063.

Sun et al., Quantitative Chemical Exchange Saturation Transfer (qCEST) MRI—RF Spillover Effect-Corrected Omega Plot for Simultaneous Determination of Labile Proton Fraction Ratio and Exchange rate, Contrast Media Mol Imaging, 2014, vol. 9, pp. 268-275.

Sun et al., A Method for Accurate pH Mapping with Chemical Exchange Saturation Transfer (CEST) MRI, Contrast Media Mol Imaging, 2016, vol. 11(3), pp. 195-202.

Takashima et al., Correlation Between T2 Relaxation Time and Intervertebral Disk Degeneration, Skeletal Radiol, 2012, vol. 41, pp. 163-167.

Van Zijl et al., Chemical Exchange Saturation Transfer (CEST): What is in a nName and What Isn't?, Magnetic Resonance in Medicine, 2011, vol. 65, pp. 927-948.

Wang et al., T1rho and T2 Relaxation Times for Lumbar Disc Degeneration: An In Vivo Comparative Study at 3.0—Tesla MRI, Eur Radiol, 2013, vol. 23, pp. 228-234.

Ward et al., A New Class of Contrast Agents for MRI Based on Proton Chemical Exchange Dependent Saturation Transfer (CEST), Journal of Magnetic Resonance, 2000, vol. 143, pp. 79-87.

Wu et al., Quantitative Chemical Exchange Saturation Transfer (qCEST) MRI—Omega Plot Analysis of RF-Spillover-Corrected Inverse CEST Ratio Asymmetry for Simultaneous Determination of Labile Proton Ratio and Exchange Rate, NMR in Biomedicine, 2015, vol. 28, pp. 376-383.

Wu et al., Quantitative Description of Radiofrequency (RF) Power-Based Ratiometric Chemical Exchange Saturation Transfer (CEST) pH Imaging, NMR in Biomedicine, 2015, vol. 28, pp. 555-565.

Zaiss et al., Inverse Z-Spectrum Analysis for Spillover-, MT-, and T1-Corrected Steady-State Pulsed CEST-MRI—Application to pH-Weighted MRI of Acute Stroke, NMR in Biomedicine, 2014, vol. 27, pp. 240-252.

\* cited by examiner

IMAGING BIOMARKERS FOR THE DIAGNOSIS AND PROGNOSIS OF BACK PAIN AND RELATED CONDITIONS

CROSS-REFERENCE TO RELATED APPLICATIONS

This application is a National Phase of International Application No. PCT/US2014/034720, filed Apr. 18, 2014, which designated the U.S. and that International Application was published under PCT Article 21(2) in English, which claims priority under 35 U.S.C. § 119(e) to U.S. Provisional Patent Application No. 61/813,996, filed Apr. 19, 2013, the contents of which are herein incorporated by reference in their entirety.

FIELD OF THE INVENTION

The present invention generally relates to imaging methods and applications thereof.

BACKGROUND

MRI is often performed on patients suffering from back pain. These scans usually reveal the presence of intervertebral disc (IVD) degeneration. Yet the link between degeneration and pain does not always exist and is poorly understood. Often MRI can detect signs of degeneration and changes of the disc structure without the presence of low back pain. In addition, in some cases pain exists, but does not originate from degenerated IVDs seen in MRI. Current standard procedure includes the use of provocative discography. In this painful procedure, a small amount of contrast agent is injected to several spinal discs in order to detect the disc from which the pain originates. Based on this test, a decision is made about which disc will be subjected to surgery. Until now, a reliable noninvasive method to detect painful discs has not been available. Therefore, there is a clear need to identify specific MRI-detectable parameters that can be indicative of pain derived from degenerated IVDs. Moreover there is a need for imaging methods that would also predict the prognosis of degenerate discs and whether they would become painful in the future. There is also a need to establish methods for the diagnosis and prognosis of related conditions affecting similar tissues

SUMMARY OF THE INVENTION

In various embodiments, the invention teaches a method for diagnosing a subject with the presence or absence of a condition characterized by tissue degeneration and/or pain. In some embodiments, the method includes imaging a region of the subject's body; detecting one or more biomarkers within the imaged region, wherein the biomarkers are selected from the group consisting of pH, glycosaminoglycan (GAG) concentration, glucose concentration, and lactate concentration; and diagnosing the subject with the presence or absence of the condition based upon the biomarkers detected within the imaged region of the subject's body. In some embodiments, the imaged region of the subject's body includes a joint or an intervertebral disc. In certain embodiments, the condition is selected from the group consisting of: intervertebral disc degeneration, discogenic pain, osteoarthritis, rheumatoid arthritis, an articular cartilage injury, tempromandibular disc degeneration and combinations thereof. In certain embodiments, the imaging includes magnetic resonance imaging. In some embodiments, the biomarkers are detected by chemical exchange saturation transfer (CEST) imaging. In certain embodiments, the biomarkers are detected by evaluating R1-rho dispersion. In some embodiments, the biomarkers include pH and/or GAG concentration. In certain embodiments, the subject is diagnosed with the condition if the biomarkers detected from imaging indicate one or more abnormal physiological states within the imaged region selected from the group consisting of low pH, low GAG concentration, low glucose, high lactate, and combinations thereof, compared to a subject without the condition. In some embodiments, the method further includes determining that an origin of the subject's pain associated with the condition is within the region of the subject's body where the abnormal physiological state is detected.

In various embodiments, the invention teaches a method for prognosing a condition associated with tissue degeneration and/or pain in a subject. In some embodiments, the method includes imaging a region of a subject's body; detecting one or more biomarkers within the imaged region, selected from the group consisting of pH, glycosaminoglycan (GAG) concentration, glucose concentration, and lactate concentration; and prognosing the condition by comparing measurements of one or more biomarkers detected within the imaged region to previous measurements of the same one or more biomarkers detected within the imaged region. In some embodiments, the condition is selected from the group consisting of: intervertebral disc degeneration, discogenic pain, osteoarthritis, rheumatoid arthritis, an articular cartilage injury, tempromandibular disc degeneration and combinations thereof. In some embodiments, the imaged region of the subject's body includes a joint or an intervertebral disc. In some embodiments, the imaging includes magnetic resonance imaging. In some embodiments, the biomarkers are detected by chemical exchange saturation transfer (CEST) imaging. In some embodiments, the biomarkers are detected by evaluating R1-rho dispersion. In certain embodiments, the biomarkers include pH and/or GAG concentration.

In various embodiments, the invention teaches a method for determining an extent of intervertebral disc (IVD) degeneration in a subject. In some embodiments, the method includes using a magnetic resonance imaging (MRI) scanner to scan a region of interest in a subject, wherein the region of interest includes an intervertebral disc; obtaining an —OH chemical exchange saturation transfer (—OH CEST) signal from the MRI scan; and determining the extent of IVD degeneration in the subject, wherein a lower —OH CEST signal, compared to normal, indicates disc degeneration, and wherein the lower the —OH CEST signal is, the greater the extent of IVD degeneration determined. In some embodiments, the MRI scan is performed by using a pulsed CEST preparation and a turbo spin echo (TSE) acquisition. In certain embodiments, the MRI scan is performed by using reduced field-of-view excitation. In some embodiments, a slice thickness for the MRI scan is selected to be small enough to avoid fat signal interference.

In various embodiments, the invention teaches a method for identifying a painful intervertebral disc (IVD) in a subject. In certain embodiments, the method includes using a magnetic resonance imaging (MRI) scanner to scan a region of interest (ROI) in a subject, wherein the ROI includes an intervertebral disc; determining $R_{1\rho}$ dispersion and —OH CEST in the ROI; and identifying a painful IVD in the subject based upon the ratio of $R_{1\rho}$ dispersion and —OH CEST (RROC), wherein a painful disc is determined if an RROC value is high compared to normal. In some embodiments, the MRI scanner is a 3.0T MRI scanner. In some embodiments, the MRI scan is performed by using reduced field-of-view excitation. In certain embodiments, a slice thickness for the MRI scan is selected to be small enough to avoid fat signal interference.

In various embodiments, the invention teaches a method for determining an extent of intervertebral disc (IVD) regeneration in a subject. In some embodiments, the method includes using a magnetic resonance imaging (MRI) scanner to scan a region of interest in a subject, wherein the region of interest includes an intervertebral disc; obtaining an —OH chemical exchange saturation transfer (—OH CEST) signal from the MRI scan; and determining the extent of IVD regeneration in the subject, wherein a higher —OH CEST signal, compared to normal, indicates disc regeneration, and wherein the higher the —OH CEST signal is, the greater the extent of IVD regeneration determined. In some embodiments, the MRI scan is performed by using a pulsed CEST preparation and a turbo spin echo (TSE) acquisition. In some embodiments, the MRI scan is performed by using reduced field-of-view excitation.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
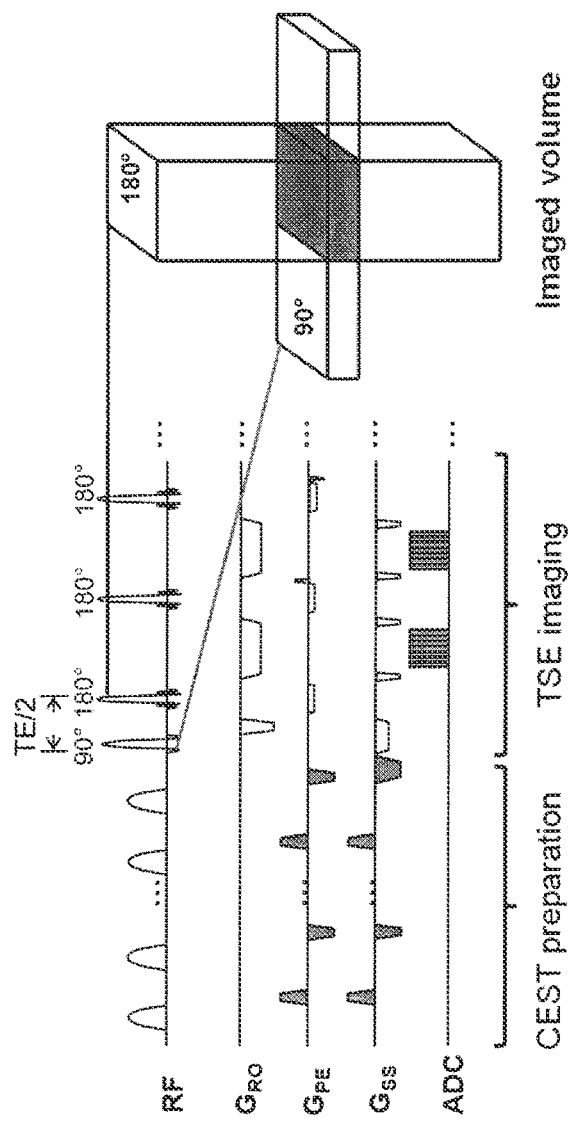
FIG. 1 demonstrates, in accordance with an embodiment of the invention, a pulse sequence for rFOV TSE CEST. rFOV was achieved by moving 180° pulses into the phase-encoding direction. The green zone indicates regions being imaged. Pulsed CSET preparation was used due to the hardware limitation of the longest RF pulse duration.

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure* 5$^{th}$ ed.; and Westbrook et al., *MRI in Practice* 4th ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions" and "disease conditions," as used herein, may include but are in no way limited to intervertebral disc degeneration, discogenic pain, osteoarthritis, rheumatoid arthritis, articular cartilage injuries, tempromandibular joint disorders, and the like.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

The inventors have developed novel methods that provide important information useful for (1) diagnosing the above-mentioned conditions, (2) monitoring the progression of the above-mentioned conditions, (3) monitoring the healing of the above-mentioned conditions, (4) identifying the origin of pain (e.g. which intervertebral disc is painful) associated with any of the above-mentioned conditions, and (5) prognosing the progression of any of the above-mentioned conditions.

The inventors' methods involve the use of various imaging techniques, described in greater detail below and in the examples set forth herein, to identify certain biomarkers, including water, pH, GAG, collagen I and II, glucose, lactate, degradation products of collagen and aggrecan, and the like. One of skill in the art would readily appreciate that the methods described herein can be performed using any clinical and investigatory magnetic resonance imaging equipment. Preferably, magnetic resonance imaging equipment with a main field of at least 3.0 Tesla is used to carry out the inventive methods described herein.

By way of background, chemical exchange saturation transfer (CEST) as a molecular imaging technique can be used to detect biochemical information related to the endogenous chemicals in the intervertebral discs (and physiologically similar tissues) such as GAG and collagen, based upon their biochemical properties, including concentration, pH, temperature, ionic strength, etc. CEST has been widely investigated in a number of studies using endogenous compounds, including amide proton transfer contrast for detection of mobile protein/peptide or pH, glycoCEST for glycogen detection, gluCEST for glutamate imaging in the brain, MICEST for myo-inositol imaging in the brain, and CrCEST for creatine imaging in muscle.

With respect to R1-rho dispersion, R1-rho values at low power (←kHz) detected by MRI are sensitive to molecular motion. In certain embodiments, the R1-rho method described herein measures the difference in R1-rho values measured at two different powers that are achievable on clinical MR scanners. The inventors' studies involving GAG solutions have shown that R1-rho dispersion is sensitive to both molecular concentration and pH, with lower pH having larger dispersion.

Because both R1-rho and CEST are related to concentration and pH, the ratio between R1-rho and CEST can cancel the effect of concentration, leaving only pH. Thus R1-rho/CEST is a biomarker for pH.

Another important imaging technique that can be used in conjunction with the inventive methods is diffusion imaging. Diffusion imaging detects signals that are related to water diffusion. A higher apparent diffusion coefficient (ADC) indicates less restrictive diffusion, whereas a lower ADC indicates the diffusion process is more restricted. Diffusion in the intervertebral disc (and physiologically similar structures) is related to its biochemical structures.

Additionally, MRI performed after contrast injection can be used to detect inflammation in a subject associated with back pain, along with other conditions described herein. More specifically, contrast enhancement patterns in patients may help to determine the origin of pain. Contrast-enhanced studies on the interverterbral discs and vertebras have also been investigated. Contrast agents that can be used can include, but are in no limited to, gadopentetate dimeglumine, gadolinium-tetraazacyclododecanetetraacetic acid, gadodiamide, gadobutrol, gadoteridol, and gadoteridol.

Importantly, the inventors' experimentation indicates that there is a direct correlation between low pH, low GAG content, low glucose, and high lactate, and pain enhancement and/or disease progression in each of the conditions described above. By using the imaging techniques described herein in conjunction with what is known about the aforementioned biomarkers, prognosis and diagnosis of a multitude of conditions associated with tissue degeneration and pain can be improved.

Therefore, in various embodiments the invention teaches a method for diagnosing a subject with the presence or absence of a condition characterized by tissue degeneration and/or pain. In certain embodiments, the method includes: (1) imaging a region of the subject's body; (2) detecting one or more biomarkers within the imaged region, wherein the biomarkers can include pH, glycosaminoglycan (GAG) concentration, glucose concentration, and lactate concentration; and (3) diagnosing the subject with the presence or absence of the condition based upon the biomarkers detected within the imaged region of the subject's body.

In some embodiments, the imaged region of the subject's body includes one or more joints or one or more intervertebral discs. In certain embodiments, the condition can include intervertebral disc degeneration, discogenic pain, osteoarthritis, rheumatoid arthritis, an articular cartilage injury, combinations thereof, tempromandibular disc degeneration and the like.

In some embodiments, the imaging performed is magnetic resonance imaging. In some embodiments, the imaging techniques performed include one or more of those described above and in the examples set forth herein. In various embodiments, the biomarkers are detected by chemical exchange saturation transfer (CEST) imaging. In some embodiments, the biomarkers are detected by evaluating R1-rho dispersion (as described in greater detail below). In certain embodiments, the biomarkers are pH and GAG concentration. In certain embodiments, the subject is diagnosed with the condition if the biomarkers detected by imaging indicate one or more abnormal physiological states within the imaged region. In certain embodiments, the abnormal physiological states can include low pH, low GAG concentration, low glucose, high lactate, and combinations thereof, compared to a subject without the condition. In some embodiments, the method further includes determining that an origin of the subject's pain associated with the condition (e.g. back pain) is within the region of the subject's body wherein the abnormal physiological state is detected.

In various embodiments, the invention teaches a method for prognosing a condition (i.e. predicting the rate of progression or improvement and/or the duration of the condition) associated with tissue degeneration and/or pain in a subject. In some embodiments, the method includes (1) imaging a region of the subject's body; (2) detecting one or more biomarkers within the imaged region, wherein the biomarkers can include pH, glycosaminoglycan (GAG) concentration, glucose concentration, and lactate concentration; and (3) prognosing the condition by comparing the measurements of the one or more biomarkers detected within the imaged region to previous measurements of the same one or more biomarkers detected within the imaged region. In some embodiments, the condition can include intervertebral disc degeneration, discogenic pain, osteoarthritis, rheumatoid arthritis, an articular cartilage injury, combinations thereof, tempromandibular disc degeneration and the like. In some embodiments, the imaged region of the subject's body includes a joint or an intervertebral disc. In some embodiments, the imaging performed is magnetic resonance imaging. In some embodiments, the imaging techniques performed include one or more of those described above and in the examples set forth herein. In various embodiments, the biomarkers are detected by chemical exchange saturation transfer (CEST) imaging. In some embodiments, the biomarkers are detected by evaluating R1-rho dispersion (as described in greater detail below). In certain embodiments, the biomarkers are pH and GAG concentration. In various embodiments, the inventive methods further include selecting an appropriate treatment for the subject to achieve beneficial results, based upon the diagnosis or prognosis ascertained by any of the inventive methods described herein.

In various embodiments, the invention teaches a method for determining an extent of intervertebral disc (IVD) degeneration in a subject. In some embodiments, the method includes using a magnetic resonance imaging (MRI) scanner to scan a region of interest in a subject, wherein the region of interest includes an intervertebral disc; obtaining an —OH chemical exchange saturation transfer (—OH CEST) signal from the MRI scan; and determining the extent of IVD degeneration in the subject, wherein a lower —OH CEST signal, compared to normal, indicates disc degeneration, and wherein the lower the —OH CEST signal is, the greater the extent of IVD degeneration that is determined. In some embodiments, the MRI scan is performed by using a pulsed CEST preparation and a turbo spin echo acquisition. In some embodiments, the MRI scan is accomplished by using reduced field-of-view excitation. In some embodiments, a slice thickness for the MRI scan is selected to be small enough to avoid fat signal interference. In some embodiments, the slice thickness is 3 mm.

In various embodiments, the invention teaches a method for identifying a painful intervertebral disc (IVD) in a subject. In some embodiments, the method includes using a magnetic resonance imaging (MRI) scanner to scan a region of interest (ROI) in a subject, wherein the ROI includes an IVD; determining $R_{1\rho}$ dispersion and —OH CEST in the ROI; and identifying a painful IVD in the subject based upon the ratio of $R_{1\rho}$ dispersion and —OH CEST (RROC), wherein a painful disc is determined if an RROC value is high compared to normal. In some embodiments, the MRI scanner is a 3.0T MRI scanner. In some embodiments, the MRI scan is accomplished by using reduced field-of-view excitation. In some embodiments, a slice thickness for the MRI scan is selected to be small enough to avoid fat signal interference.

One skilled in the art will recognize many methods and materials similar or equivalent to those described herein, which could be used in the practice of the present invention. Indeed, the present invention is in no way limited to the methods and materials described.

EXAMPLES

Experiments I

Reliable Chemical Exchange Saturation Transfer Imaging of Human Lumbar Intervertebral Discs Using Reduced-Field-of-View Turbo-Spin-Echo at 3.0 Tesla Example 1

Introduction

As indicated above, low back pain (LBP) is a disease with wide prevalence and significant burden. In the adult population, back pain of at least moderate intensity and duration has an annual incidence of 10-15%. It adversely influences the lives of those affected, resulting in suffering and disability, and poses enormous economic burden on individuals and the society. Back pain is associated with natural degenerative process of the intervertebral disc (IVD), which is the largest avascular structure in the human body. The IVD is composed of: (1) the nucleus pulposus (NP), a gel-like structure in the center of the disc rich in proteoglycan [protein core with glycosaminoglycans (GAGs)]; (2) the annulus fibrousus (AF), a collagenous zone around the NP; and (3) the cartilaginous end-plate (EP) on top and bottom (3). GAGs play a critical role in supporting IVD functions including generating hydrostatic pressure to resist loading by binding water. The loss of GAGs is coupled with changes in biochemical and biomechanical properties (4), thus is a good imaging biomarker. Quantifying changes in GAG concentration can provide an avenue of monitoring disease progression and understanding the pathophysiology of disc degeneration.

Disc degeneration has been assessed with various MR techniques. $T_2$ weighted MRI is routinely used in evaluating degeneration by morphological abnormalities. Pfirrmann grading classifies IVD degeneration into 4 degrees based on sagittal $T_2$ weighted images. Features such as decreased disc height and reduced distinction between NP and AF are indicators of degeneration. Schneiderman's classification based on $T_2$ weighted images is also a prevailing grading method. Contrast-enhanced MRI has been investigated to study the status of endplate on perfusion in the normal and degenerated discs, offering a noninvasive method to identify endplate cartilage damage. Other MR research includes spectroscopy, $T1_\rho$ imaging, diffusion imaging, and Na-imaging attempt to link MR measurements with IVD degeneration. However, these MR methods either rely on subjective evaluation thus failing to provide objective quantitative measurement, or fail to provide reliable information on GAGs concentration available in a clinical setting.

Chemical exchange saturation transfer (CEST) imaging is sensitive to loss of GAGs. In CEST imaging frequency selective radiofrequency (RF) irradiation applied for a few seconds on such exchangeable protons leads to water pool signal reduction with an amplitude that is typically hundreds to millions times higher than that of the solute proton. A number of studies have investigated the use of endogenous compounds for CEST imaging, including amide proton transfer contrast for pH detection, glycoCEST for glycogen detection, gluCEST for glutamate imaging in the brain. Having an essential role in disc degeneration, GAGs have extensive exchangeable protons such as amide protons (—NH) at +3.2 ppm and hydroxyl protons (—OH) at around +1.0 ppm that are detectable by CEST. Ex vivo study has demonstrated a relationship between the fast-exchanging —OH CEST signal and GAG concentration (See Saar et al. Assessment of glycosaminoglycan concentration changes in the intervertebral disc via chemical exchange saturation transfer NMR Biomed. 2012; 25(2):255-261, which is incorporated by reference herein in its entirety as though fully set forth). A study by Kim et al. demonstrated the feasibility of transforming the above technique into in vivo IVDs at 3.0 Tesla (See Kim et al. Assessment of glycosaminoglycan distribution in human lumbar intervertebral discs using chemical exchange saturation transfer at 3 T: feasibility and initial experience. NMR Biomed, 2011; 24(9): 1137-1144, which is incorporated herein by reference as though fully set forth). The used sequence is composed of CEST preparation and a turbo-spin-echo (TSE) acquisition, to leverage TSE's high signal-to-noise (SNR) ratio and insensitivity to field inhomogeneity. In a later study decreasing CEST signals were related to increasing grade of degeneration in volunteers, with —OH CEST signal being 7.17% and 6.00% for Schneiderman grade 0 and 1 discs, respectively. Clearly it is desirable to have a technique that can reliably measure CEST signal and to reliably differentiate its tiny changes, which reflect the degree of degeneration.

In vivo application of the current TSE CEST techniques may suffer from artifacts that reduce CEST imaging reliability and undermines its clinical applicability. These artifacts are likely caused by motion of intestine that may appear both anterior and lateral to a lumbar IVD. Bowel movement is well known to induce artifacts, and certain drugs such as glucagon is administrated clinically to slow it. When a same axial TSE image is repeatedly scanned, clear signal variations can be observed in the IVD. An axial lumbar IVD CEST scan that usually takes at least several minutes is inevitably prone to such artifacts. Since the artifact-contaminated images could eventually lead to inaccurate CEST signal measurement, a TSE CEST technique to image IVD in vivo with reduced artifacts from bowel movement represents a significant and useful advancement.

The reduced-field-of-view (rFOV) excitation strategy has previously been utilized to generate MR signals from a region of interest (ROI) only, and moving structures out of the ROI will not introduce any motion artifacts to the reconstructed images. Given its compatibility with the TSE acquisition method, rFOV is an excellent solution to improve TSE CEST imaging. As discussed in greater detail below, the inventors developed an rFOV-based TSE technique for in vivo IVD CEST imaging at 3.0T. The proposed method was first validated on concentration-controlled GAG phantom, and was then compared with the conventionally used TSE (referred to as 'conventional TSE' hereafter) technique for CEST imaging on nine volunteers.

Example 2

Materials and Methods

Phantom

To verify the relationship between GAG concentration and CEST signal, four samples of GAGs with concentrations of 50, 100, 150, and 200 mM respectively were prepared from chondroitin sulphate A (Aldrich-Sigma, St. Louis, Mo., USA) in a standard solution of phosphate-buffered saline. All pHs were titrated to 7.0. The concentration refers to the number of disaccharide units in GAGs. At the time of imaging the GAG samples were individually placed in a gadolinium-doped water bath to reduce its $T_1$.

Human Subjects

Nine healthy volunteers (3 female, 6 male; mean age 39.1±11.9) with no symptoms related to the spine and no history of spine disease were recruited.

Pulse Sequence

A 2D rFOV TSE CEST sequence (FIG. 1) was implemented. To achieve rFOV, gradients of the 180° refocusing pulses in TSE were moved from the slice-encoding direction to the phase-encoding direction with their magnitude modified accordingly based on the desired reduced FOV size. A high time-bandwidth product of 10 was used for 180° radio-frequency (RF) pulses to achieve better slice profile along the phase-encoding direction. In contrary to the conventional TSE, the number of k-space lines needed to obtain an image was largely reduced and all k-space lines were acquired following a single excitation. Centric-encoding was used to maximize CEST signal for central k-space lines that are responsible for the majority of image contrast, as CEST effects decays based on T1 time after preparation.

CEST-preparation was achieved by using a train of 8 Gaussian pulses of 1440° and a 50% duty cycle, with each pulse lasting 90 ms. To correct for $B_0$ field inhomogeneity, the WASSR method (See Kim et al. Water saturation shift referencing (WASSR) for chemical exchange saturation transfer (CEST) experiments. Magn. Reson. Med. 2009; 61(6):1441-1450, which is incorporated herein by reference in its entirety as though fully set forth) was employed to determine water pool resonance frequency by using the same CEST pulse sequence with decreased saturation amplitude and duration. WASSR was achieved by two 40°, 30 ms Gaussian pulses. Spoiler gradients were inserted after the CEST/WASSR preparation to spoil any residual transverse magnetization. Shimming and reference frequency remained unchanged throughout CEST and WASSR acquisition. In both phantom and human studies acquisitions included 31 CEST images with saturation offsets evenly distributed between −4.5 ppm and +4.5 ppm, one image without saturation ($S_0$), and 11 WASSR images with offsets evenly distributed between −1.0 ppm and +1.0 ppm. This WASSR offset frequency range was sufficient to cover maximum frequency shift in phantoms and IVDs after careful shimming.

MRI Acquisitions

All images were acquired on a 3.0 T clinical scanner (Magnetom Verio, Siemens Medical Solutions, Erlangen, Germany). RF was transmitted using the body coil, which supports a maximum RF duration of 100 ms. A 24-elements spine coil was used for signal reception in both phantom and human scans.

Single-slice GAG phantom imaging in the axial plane was conducted using rFOV TSE CEST. Parameters were:

TE/TR=9/2500 ms, slice thickness=5 mm, bandwidth=300 Hz/pixel, FOV=47×180 mm$^2$, echo-train-length (ETL)=34, matrix=34×128, 3 averages.

Following localizer and sagittal T$_2$-weighted TSE acquisitions, in each of the nine volunteers one L3/L4 axial IVD slice was acquired with the same image plane and slice thickness for both conventional TSE and rFOV TSE CEST imaging. Both techniques were repeated twice in a random order to test their reproducibility. Common imaging parameters between techniques were: TE/TR=9/2500 ms, slice thickness=3 mm, bandwidth=298 Hz/pixel, ETL=30. For conventional TSE parameters were: FOV=230×230 mm$^2$, matrix=90×128, 1 average. For rFOV TSE, a reduced FOV along phase-encoding direction (left to right) was chosen to cover the disc. Other parameters were: FOV=68×230 mm$^2$, matrix=30×128, 3 averages were used to reach the same imaging time as conventional TSE. Total imaging time for either method (including WASSR) is 5.3 mins. In one volunteer (41Y/F) with obvious degeneration rFOV TSE CEST was also performed on L2/L3, L3/L4, L4/L5, and L5/S1 discs, to examine its ability in identifying disc degeneration.

Example 3

Data Analysis

All CEST images were first normalized by S$_0$ and corrected for B$_0$ inhomogeneity pixel by pixel. The pixel-by-pixel B$_0$ frequency shift was determined in WASSR by fitting a Lorentzian line shape (See Zaiss et al. Quantitative separation of CEST effect from magnetization transfer and spillover effects by Lorentzian-linefit analysis of z-spectra. J. Magn. Reson. 2011; 211(2):149-155, which is incorporated by reference herein in its entirety as though fully set forth) in a 0.8 ppm frequency range which has substantial saturation. Then the curve was spline interpolated to produce the Z-spectrum (CEST vs. offset-frequency curve). Data at ±4.5 ppm were excluded from subsequent analysis. Magnetization transfer asymmetry ratio (MTR$_{asym}$) for each pixel was calculated as:

$$MTR_{asym}(\Delta\omega) = \frac{S(-\Delta\omega) - S(\Delta\omega)}{S_0}, \quad [1]$$

where $\Delta\omega$ is the frequency offset of the saturation pulse, $S(\pm\Delta\omega)$ is the CEST signal intensity at the frequency offset $+\Delta\omega$ and $-\Delta\omega$ respectively.

For each phantom, one ROI containing at least 120 pixels inside the GAG region was first drawn, then MTR$_{asym}$ values were averaged within the ROI. Since —OH protons resonant around +1.0 ppm downfield from water pool, the average MTR$_{asym}$ signal between 0.5 ppm and 1.5 ppm were integrated in order to quantify —OH CEST (See Kim et al. Assessment of glycosaminoglycan distribution in human lumbar intervertebral discs using chemical exchange saturation transfer at 3T: feasibility and initial experience. NMR Biomed, 2011; 24(9): 1137-1144, which is incorporated herein by reference as though fully set forth). Linear regression was used to examine the linearity between —OH CEST and GAG concentration.

For human images, one ROI containing nucleus pulposus was drawn by an experienced researcher in the center of the IVD and the average MTR$_{asym}$ was calculated. Since bowel movement happens independently with MRI acquisition, bowel movement artifacts lead to 'random noises' that add upon to the MTR$_{asym}$ curve. When acquisition was repeated twice, significant differences were expected between MTR$_{asym}$ curves obtained from these two acquisitions. To quantify the difference between them, the Sum of Absolute Difference (SAD) value over all MTR$_{asym}$ data points was calculated as follows:

$$SAD(MTR_{asym}) = \sum_{i=1}^{N} |MTR_{asym1}(\Delta\omega_i) - MTR_{asym2}(\Delta\omega_i)|. \quad [2]$$

where N (=14 in this case) is the number of data points in a MTR$_{asym}$ curve, MTR$_{asym1}$ and MTR$_{asym2}$ are MTR$_{asym}$ curves from the first and second acquisition respectively, and $\Delta\omega_i$ is the offset frequency of the corresponding data points. Larger SAD indicates more variation between two acquisitions of a same MTR$_{asym}$ curve, which then reflects more bowel movement artifacts. Similarly a smaller SAD indicates less bowel movement artifacts.

Pfirrmann grading was also performed based on sagittal T2-weighted TSE image in the one volunteer with obvious IVD degeneration, by an experienced researcher. A grade (I, II, III or IV) was assigned to each disc.

Post processing was performed with a custom-written program in Matlab (The Mathworks, Natick, Mass.). Paired-t test was used to test SAD value differences between conventional TSE and rFOV TSE CEST with the significant level defined at $\alpha$=0.05 using SPSS v. 16.0 (SPSS, Chicago, Ill.).

Example 4

Results

Figure 2:
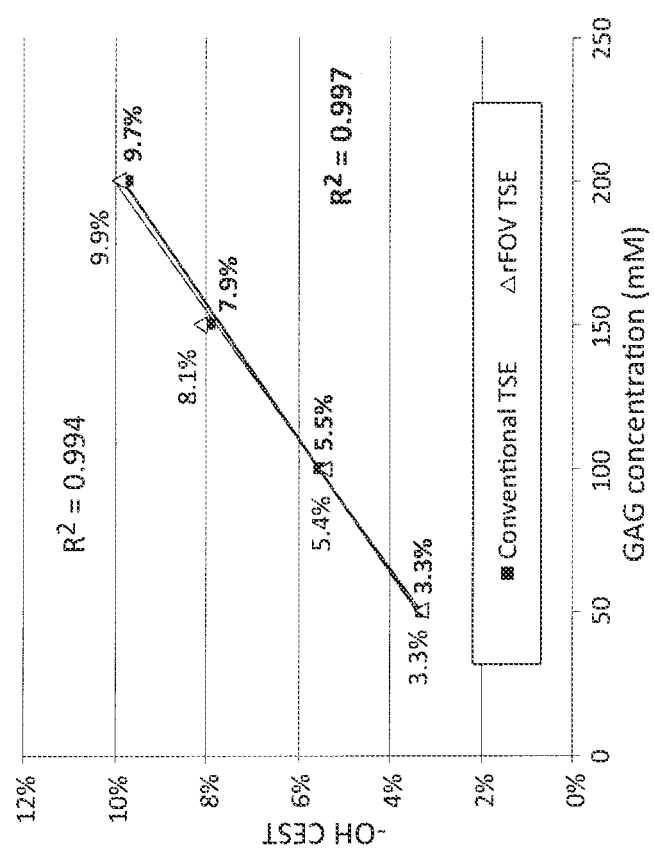
FIG. 2 demonstrates, in accordance with an embodiment of the invention, a GAG phantom study demonstrates a good linear relationship ($R^2$=0.997 and 0.994) between GAG concentration and the measured —OH CEST signal by conventional TSE and rFOV TSE CEST, respectively. The —OH CEST signal is calculated by integrating $MTR_{asym}$ between 0.5 ppm and 1.5 ppm.

The phantom study (FIG. 2) showed that —OH CEST was highly correlated with GAG concentration (R$^2$=0.997). This indicates that the proposed rFOV TSE CEST is linearly related to GAG concentration, and can potentially serve as a biomarker for GAG concentration and IVD degeneration.

Figure 3:
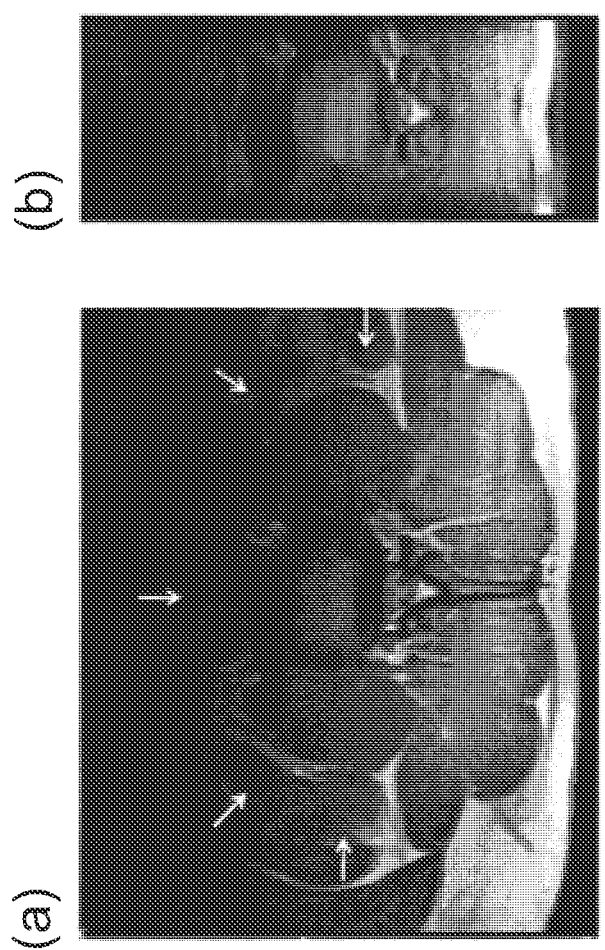
FIG. 3 demonstrates, in accordance with an embodiment of the invention, typical conventional TSE (a) and rFOV TSE (b) images from a healthy volunteer. The white arrows in (a) indicate regions with bowel movements. In TSE these movements could lead to artifacts that compromise IVD CEST imaging reliability. With the rFOV technique, the image in (b) is almost free of such artifacts.

FIG. 3 shows typical in vivo IVD images obtained from conventional TSE and rFOV TSE of a same disc. Arrows in FIG. 3a illustrates regions with bowel movement that causes artifacts. In FIG. 3b the rFOV technique only imaged regions slightly larger than the disc in phase-encoding direction while excluding signal contributions from outside the FOV, thus reduces bowel movement artifacts.

Figure 4:
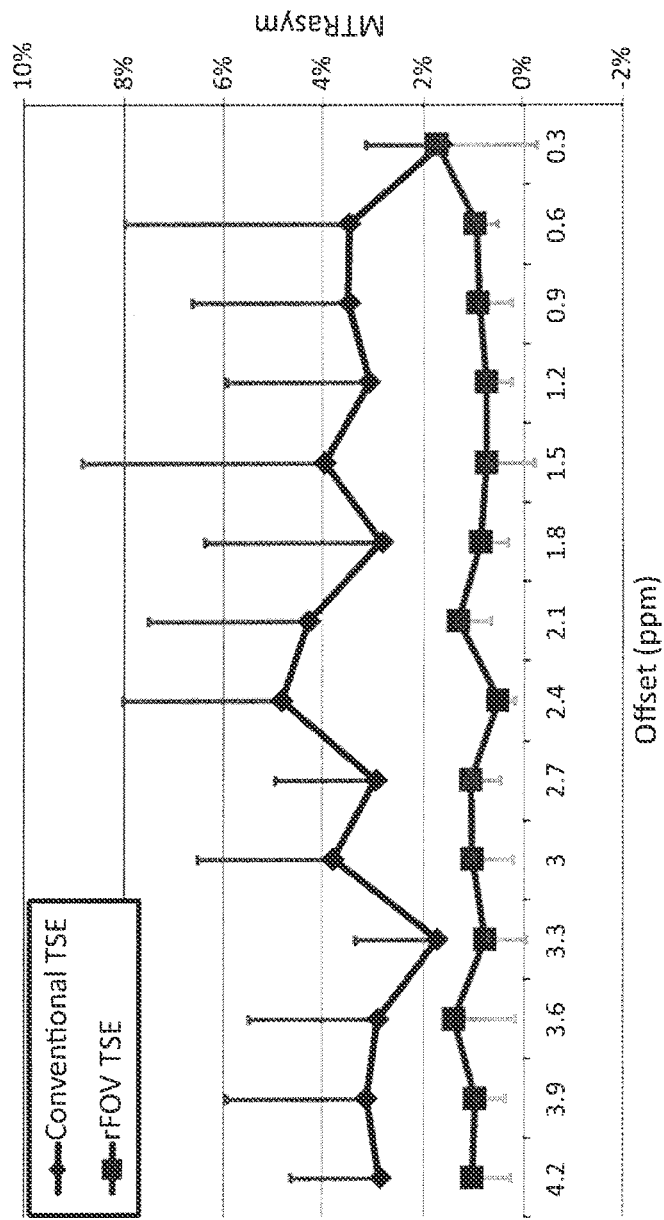
FIG. 4 demonstrates, in accordance with an embodiment of the invention, the absolute difference between the $MTR_{asym}$ curves from two acquisitions, for both conventional FOV and rFOV TSE CEST imaging, from all healthy volunteers. Data were represented as mean±standard deviation (error bars indicate standard deviation). Compared with conventional TSE, rFOV TSE $MTR_{asym}$ has smaller differences when repeated, thus it is a more reproducible technique.
Figure 5:
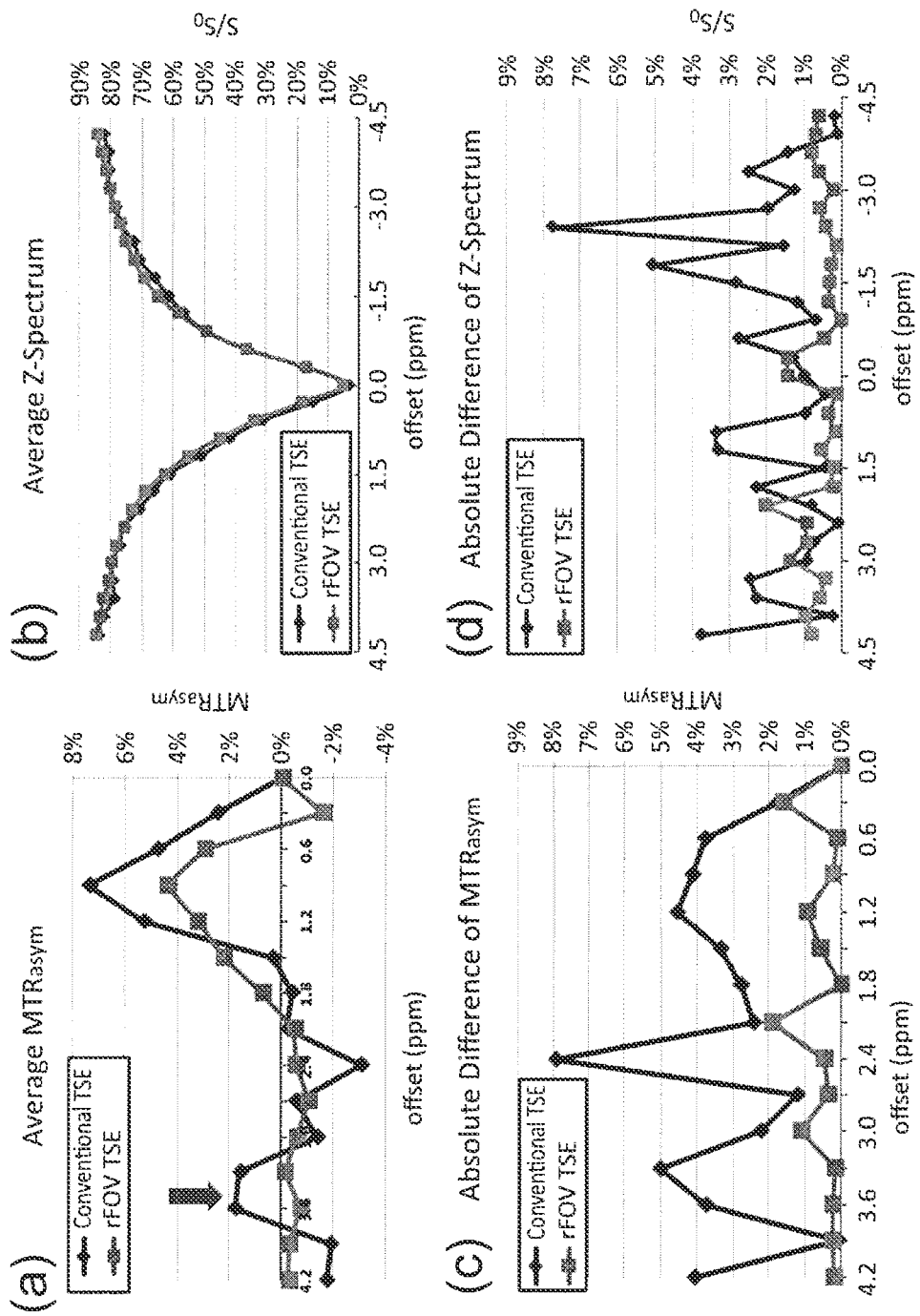
FIG. 5 demonstrates, in accordance with an embodiment of the invention, (a) the average of and (c) the absolute difference between the $MTR_{asym}$ curves from two acquisitions, for both conventional FOV and rFOV TSE CEST imaging, from a typical healthy volunteer. (b), (d) the average and absolute difference of the corresponding Z-spectra, respectively. In this case the 'peak' around 3.5 ppm in conventional TSE as shown by the arrow in (a) could be misinterpreted as from —NH protons, but in fact could also possibly be a result of bowel movement artifacts as reflected by the large variation between repetitions in (c) around 3.5 ppm.

The difference between these two CEST imaging techniques can be better appreciated in FIG. 4, where it shows the average absolute difference of the MTR$_{asym}$ curves of two acquisitions, for all volunteers. rFOV TSE demonstrated smaller average difference between acquisitions over all offset frequencies, indicating rFOV is a more reliable technique that can consistently reproduce CEST measurements in vivo. Also the variations of such differences were smaller across volunteers, as shown by the shorter error bars of rFOV compared with those of conventional TSE. In the inventors' experiments certain volunteers had more bowel movement than others. With the rFOV that largely reduces movement artifacts, it is expected the contribution of such artifacts to the absolute difference is reduced accordingly. This explains the smaller variation of the absolute difference across volunteers. FIG. 5 shows one example where conventional TSE might lead to erroneous interpretation of CEST data. A 'peak' of about 2% could be identified at around 3.5 ppm in (a), yet this is likely caused by artifacts, as justified by the large difference of about 4% at the same offset in (b). This 'peak' could easily be wrongly attributed to —NH protons that resonant around a similar frequency, while with the improved reliability of rFOV technique there is no such concern.

Quantitative analysis also demonstrated the improved reproducibility of rFOV. With only nine volunteers, rFOV CEST showed (Table 1) significantly decreased SAD compared to conventional TSE (0.14 vs 0.45, p=0.002<0.05). The mean $MTR_{asym}$ absolute difference of a single offset frequency was 0.94% and 3.01% for rFOV and conventional TSE CEST respectively.

Figure 6:
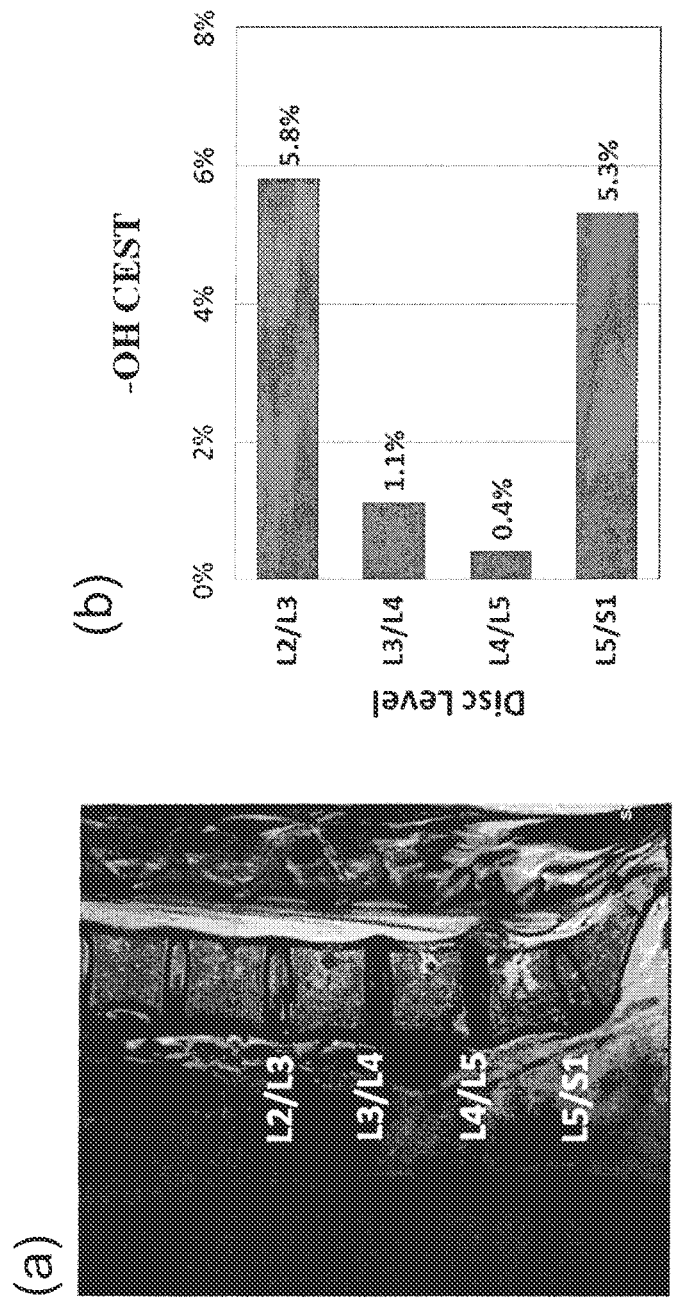
FIG. 6 demonstrates, in accordance with an embodiment of the invention, imaging of IVD degeneration by rFOV TSE CEST in a healthy volunteer (41Y/F) with disc degeneration. (a) The sagittal $T_2$-weighted TSE image. (b) —OH CEST signals for discs from L2/L3 down to L5/S1. Pfirrmann grade III discs (L3/L4, L4/L5) have substantially lower —OH CEST signal than grade II discs (L2/L3, L5/S1).
Figure 7:
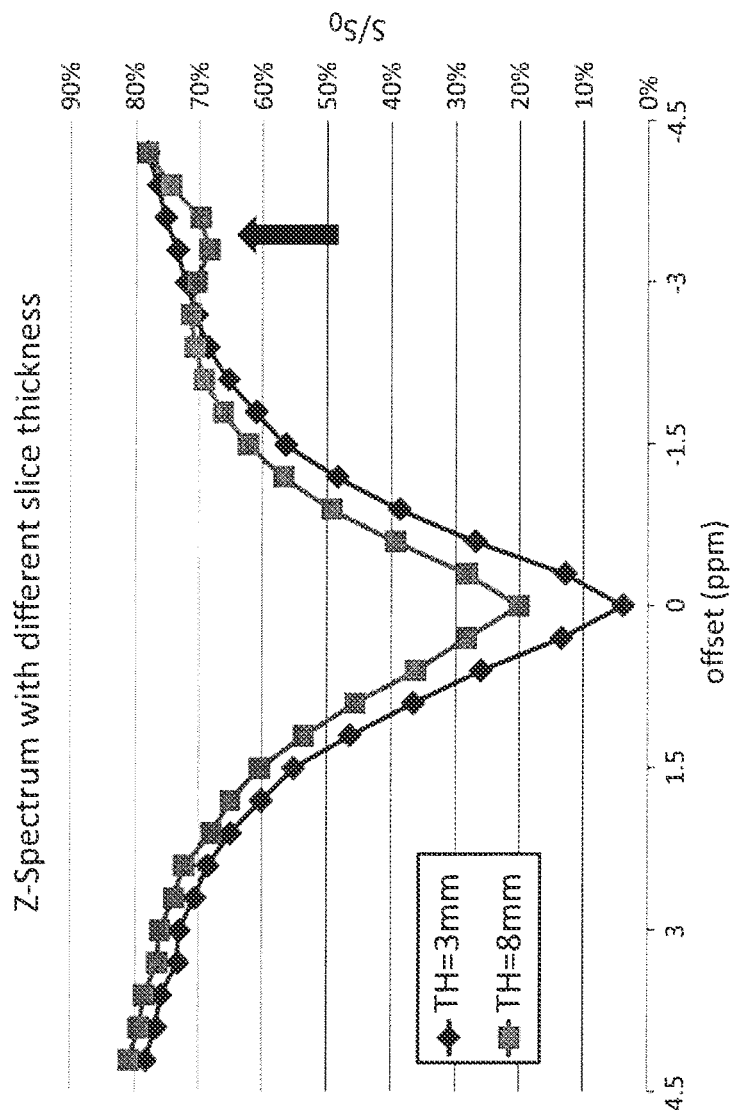
FIG. 7 demonstrates, in accordance with an embodiment of the invention, the Z-spectrum of a healthy volunteer (36Y/M) with rFOV TSE CEST when acquired with a slice thickness of 3 mm and 8 mm, respectively. The arrow points to a 'dip' caused by a fat signal from interference of surrounding bone tissue.

The feasibility of rFOV TSE CEST in imaging IVD degeneration is illustrated on a human subject in FIG. 6. Out of the four discs studied, L2/L3 and L5/S1 were classified as Pfirrmann grade II, and L3/L4 and L4/L5 were classified as grade III discs. It is clear in FIG. 6(b) that the more degenerated discs (L3/L4 and L4/L5) have substantially lower —OH CEST signal compared with the less degenerated discs. The inventive rFOV TSE CEST can serve as a reliable MR technique to image IVD degeneration.

TABLE 1

Sum of absolute difference over all $MTR_{asym}$ curve data points between two acquisitions for conventional TSE and rFOV TSE CEST.

| Volunteer number | SAD between two acquisitions | |
| --- | --- | --- |
| | Conventional TSE | rFOV TSE |
| 1 | 0.485 | 0.160 |
| 2 | 0.170 | 0.134 |
| 3 | 0.977 | 0.293 |
| 4 | 0.736 | 0.135 |
| 5 | 0.337 | 0.089 |
| 6 | 0.289 | 0.068 |
| 7 | 0.288 | 0.095 |
| 8 | 0.320 | 0.210 |
| 9 | 0.470 | 0.082 |
| Average* | 0.453 ± 0.255 | 0.140 ± 0.072 | p = 0.002 < 0.05.
*Average expressed as mean ± standard deviation.

Example 5

Discussion

The experiments described herein demonstrate the rFOV TSE technique in vivo IVD CEST imaging can be achieved reliably, which allows for better quantification of GAG concentration and imaging of IVD degeneration. The technique was verified on GAG phantoms and on nine healthy volunteers. IVD —OH CEST typically has small $MTR_{asym}$ signal of no more than 8-10%. The —OH CEST signal difference between a Schneiderman grade 0 and 1 disc is only 1.17%. Thus it is crucial to reliably detect this signal with high accuracy. IVD imaging by conventional TSE suffers from bowel movement artifacts that result in low reproducibility and sometimes lead to inaccurate CEST measurement. On the other hand, rFOV TSE CEST performs significantly better than conventional TSE CEST, which permits accurate quantification of —OH CEST, and potentially detects even smaller signals from other exchangeable protons such as —NH proton.

Phantom and volunteer CEST measurements were in line with those previously published by Kim et. al (See Kim et al. Assessment of glycosaminoglycan distribution in human lumbar intervertebral discs using chemical exchange saturation transfer at 3 T: feasibility and initial experience. NMR Biomed, 2011; 24(9): 1137-1144, which is incorporated herein by reference as though fully set forth). Both studies demonstrated a linear relationship between GAG concentrations and —OH CEST signal as well as reduced —OH CEST in IVDs with degeneration. Besides the rFOV technique, certain other improvements have been made over the previous study as well. First, a thinner slice (3 mm vs. 8 mm) was used. With an 8 mm-thick-slice a significant 'dip' (could be as high as 20%) at around -3.2 ppm in the Z-spectrum was observed. While not wishing to be bound by any one particular theory, this signal decrease could come from saturation of fat signal in the vertebrae above and below the imaged IVD where the bone marrow is known to be rich in fat. The inclusion of such fat signal is likely caused by slice-profile imperfection in slice-selection direction. As slice thickness increased from 3 mm to 8 mm gradually, the saturation at -3.2 ppm increased in magnitude in a disc with normal height. This fat saturation overlay with the nuclear Overhauser effect (NOE) that also takes place at -3.2 ppm, and further complicates $MTR_{asym}$ analysis. Imaging of severely degenerated human IVDs may pose additional challenges as such discs are usually associated with decreased height. Thus it is important to keep a slice thickness that is thin enough to avoid fat signal interference from vertebrae, while thick enough to have good image quality. The 3 mm thickness was determined empirically in the study described herein. Alternatively, one could combine the use of a thick slice with a short chemical shift-selective fat suppression pulse right before TSE acquisition, yet the notorious magnetic field inhomogeneity issues in the spine could deteriorate fat saturation effect, complicating CEST signal analysis. Second, pulsed CEST preparation was used instead of the 500 ms continuous CEST preparation. The longest RF pulse duration is usually constrained by hardware limitation on clinical scanners. For instance, on the inventors' scanner the longest RF pulse duration is limited to 100 ms, which is shorter than the preparation time on the order of seconds that is required to achieve substantial CEST effect. There is also a hardware limit on the maximum duty cycle allowed for CEST imaging. Admittedly in certain applications such as knee imaging a higher duty cycle may become available by the use of special coil, yet in some embodiments, such as for IVD imaging, a maximum of 50% duty cycle is imposed by body coil transmission in the inventors' system. The pulsed CEST preparation scheme described herein can be easily implemented on any clinical scanners, allowing reliable GAG imaging.

The improved reliability of rFOV opens the possibility of imaging other exchangeable protons. Merely by way of non-limiting example, —NH protons in IVDs are of particular interests. In the brain —NH CEST has been used to image Ischemic acidosis and tumors. The possible feasibility of —NH CEST in assessing breast tumor chemotherapy response is also studied. Considering IVD is also rich in —NH protons, it is likely that —NH CEST could provide additional information in assessing disc degeneration. GAG —NH CEST signal was observed in bovine disc and cartilage with a typical magnitude much less than —OH. In short, the inventors believe imaging of —NH is of great potential value.

Several other techniques can also be used to reduce bowel movement artifacts. Saturation band is clinically used to reduce bowel movement artifacts in spine imaging. However, this technique failed to provide adequate bowel movement suppression in the inventors' test study (data not shown), which is likely due to that the small CEST effect is extremely sensitive to artifacts. Although in other applications saturation band may work well to provide image quality that is good enough, in CEST imaging it failed to work for the purpose. 2D spatially-selective RF excitation can excite spins within a given rFOV, thus avoid motion artifacts from outer regions. Yet this technique comes with costs of longer RF duration and higher energy deposition, and remains largely investigational. The administration of glucagon can reduce bowel movement, but it nevertheless suffers from various side-effects.

In the inventors' study, the number of RF pulses and flip angle were chosen empirically through a series of experimental scans. Rigid parameter optimization by both simulation and in vivo scans would be useful to maximize the measured CEST signal. The maximum possible duty cycle of 50% was used. The average CEST power expressed as a continuous-wave equivalent (36) is around 0.8 μT. The inventors' studies indicate decreased —OH CEST is observed as the degree of IVD degeneration increases. Insensitivity to bowel movement in rFOV TSE CEST comes with a cost of higher energy deposition. Although still well below FDA standards, the high time-bandwidth product of 10 used for better RF profile increased specific absorption rate (SAR). Since CEST preparation is already SAR intensive, caution is suggested in executing such sequences.

Example 6

Conclusion

In sum, the inventors incorporated the rFOV technique into TSE CEST acquisition to reliably image the IVD in vivo, by reducing bowel movement artifacts. The inventors' technique demonstrated significantly better reproducibility when compared with the conventionally used sequence, which allows for quantitative IVD degeneration imaging in a clinical setting, and could also allow future research on CEST effect from exchangeable protons with smaller magnitude such as —NH. One of skill in the art would readily appreciate that this novel technique is also applicable to other anatomies where rFOV effect is desired either to remove motion artifacts or to avoid aliasing such as the lungs, heart and major blood vessels.

The equation numbers referenced in the section below refer solely to the equations of Experiments II.

Experiments II

Detection of Low Back Pain Using pH Level-Dependent Imaging of the Intervertebral Disc Using the Ratio of $R_{1\rho}$ Dispersion and —OH Chemical Exchange Saturation Transfer (RROC)

Example 7

Introduction

Further to the introduction provided in the section above, NP is rich in PG, which has numerous GAG chains of chondroitin sulfate and keratan sulfate attached. Metabolism of disc cells is mainly through anaerobic glycolysis, leading to significant lactate production. Diffusion is the primary pathway for supply of nutrients such as glucose and oxygen to disc cells, as well as the depletion of metabolic wastes such as lactate. The lactate concentration in the center of the disc can be up to 8-10 times higher than in the plasma. As a consequence, disc pH is acidic.

Magnetic resonance spectroscopy (MRS) has been exploited to non-invasively assess lactate in IVD. Zuo et al. (See Zuo et al. Assessment of intervertebral disc degeneration with magnetic resonance single-voxel spectroscopy. Magn. Reson Med 2009; 62:1140-1146, which is incorporated by reference herein in its entirety as though fully set forth) demonstrated the feasibility of acquiring localized $^1$H spectra on a 3.0T scanner on intact bovine and human cadaveric discs to quantify lactate, the source of low pH. A later study (See Zuo et al. In vivo intervertebral disc characterization using magnetic resonance spectroscopy and T1 rho imaging: association with discography and Oswestry Disability Index and Short Form-36 Health Survey. Spine (Phila Pa. 1976) 2012; 37:214-221, which is incorporated by reference herein in its entirety as though fully set forth) characterized IVD in vivo. Importantly, although a significantly elevated water/PG area ratio was found in painful discs based on discography, no lactate peak was reliably detected. In vivo MRS suffers from several limitations that prohibit lactate detection: limited signal-to-noise ratio (SNR), physiological motion, bone susceptibility induced line broadening, difficulty in differentiating lactate from lipid peaks as their resonance frequencies are close, collapsed disc space in certain patients, etc.

Recently magnetic resonance imaging (MRI) has been exploited to non-invasively assess pH in IVD. Melkus et al. adopted both endogenous and exogenous approaches to investigate the pH dependence of chemical exchange saturation transfer (CEST) in porcine IVDs (See Melkus et al. Ex vivo porcine model to measure pH dependence of chemical exchange saturation transfer effect of glycosaminoglycan in the intervertebral disc. Magn Reson Med 2013. Doi:10.1002/mrm.24838, which is incorporated herein by reference as though fully set forth). Endogenous CEST of hydroxyl (—OH) protons on GAGs (gagCEST) demonstrated pH sensitivity on phantoms and ex vivo porcine IVD specimens at 7.0 Tesla. CEST of exogenous computed tomography (CT) contrast agent Iopromide that was injected into the discs also demonstrated pH imaging potential. Iopromide, together with similar types of contrast agents such as Iopamidol and Iohexol, has been investigated as pH probes in a number of applications such as mice kidney, mice tumor, and human bladder. While both the endogenous and exogenous IVD pH imaging approaches are promising, significant limitations remain. First, the existing gagCEST pH measurement approach is confounded by GAG concentration. Since both pH and GAG concentration will affect gagCEST signal, further correction is needed. Second, despite the feasibility demonstrated at 7.0 Tesla, no efforts were made to translate the techniques onto 1.5 or 3.0 Tesla. Third, the CT contrast agent approach may be unsuitable for in vivo imaging. Diffusion is the primary pathway for exogenous contrast agent to enter the IVD, the largest avascular structure in human body. In a normal disc it may take several hours for exogenous contrast agent to diffuse into central NP. Such a long waiting time may hamper the technique's applicability in a clinical setting. Moreover, to quantify the amide CEST signal at 4.2 ppm and 5.6 ppm, high-enough Iopromide concentration in the IVD is required. If Iopromide is to be administrated intravenously, a prohibitively high dose may be needed so that enough contrast enters the IVD, which could elicit safety concerns. Direct injection of Iopromide into the disc could also work on humans, yet as an invasive technique it will potentially cause side effects including pain and infection. These contrast delivery issues may challenge the application of exogenous CT contrast agents for pH imaging of humans.

With these issues in mind, the inventors have developed an MRI technique for in vivo IVD pH level-dependent imaging on a 3.0 Tesla clinical scanner, without using exogenous contrast agents. The technique employs the ratio of $R_{1\rho}$ dispersion and —OH CEST (RROC). It was verified by numerical simulations and studies on chondroitin sulphate phantoms and ex vivo porcine spines. The technique's potential in diagnosing painful discs was then explored in a study involving LBP patients.

Example 8

Theory

CEST

Pulsed-CEST effect can be approximated by the analytical solution of continuous-wave CEST signal (See Zu et al. Optimizing pulsed chemical exchange saturation transfer imaging sequences. Magn Reson Med 2011:66:1100-1108, which is incorporated herein by reference in its entirety as though fully set forth). Considering a two-pool (labile and water pool) exchange model with no back exchange of saturated protons or direct saturation (DS) on water protons, the analytical solution for continuous-wave CEST is shown to be:

$$CEST = f \cdot \alpha \cdot k_{sw} \cdot T_{1w}(1 - e^{-t_{sat}/T_{1w}}) \qquad [1]$$

where f is the relative concentration of labile protons, a is the saturation coefficient and is a function of exchange rate $k_{sw}$, $T_{1w}$ is the longitudinal relaxation rate of water pool, and $t_{sat}$ is saturation time. According to Equation. 1 the measured CEST effect is proportional to concentration f, and is a function of exchange rate $k_{sw}$, which in turn is a function of pH. It is worth mentioning that the above assumptions are not completely valid for —OH CEST at 3.0T, as back exchange and DS can't be neglected. Nevertheless when the concentration is small enough, as an approximation the above equation provides valuable insights on CEST signal's relationship with pH and concentration. In fact, a roughly linear relationship between —OH CEST and GAG concentration was discovered on phantoms.

$R_{1\rho}$ Dispersion $R_{1\rho}$ (the longitudinal relaxation rate in the rotating frame) dispersion, the dependence of $R_{1\rho}$ on spin-lock amplitude (SLA), is sensitive to chemical exchanges with intermediate exchange rates. Considering a two-pool exchange model (labile and water pool) with highly unequal population (labile proton concentration $p_1 \ll$ water pool concentration $p_w$), $R_{1\rho}$ can be obtained as:

$$R_{1\rho} = R_1 \cdot \cos^2\theta + \left(R_2 + \frac{p_1 \cdot \delta^2 \cdot k_{ex}}{(\delta - \Omega)^2 + \omega_1^2 + k_{ex}^2}\right) \cdot \sin^2\theta \qquad [2]$$

where $R_1$ is the longitudinal relaxation rate of water, $R_2$ is the intrinsic water transverse relaxation rate in absence of chemical exchange, $\delta$ is the chemical shift of labile pool relative to water pool, $k_{ex}$ is the exchange rate between the two pools. $\theta = \arctan(\omega_1/\Omega)$ is the angle between effective magnetization and Z-axis, where $\omega_1$ is the SLA and $\Omega$ is the frequency offset. In addition, the exchange rate from water to labile pool ($k_w$) and labile to water pool ($k_1$) satisfy $p_w \cdot k_w = p_1 \cdot k_{labile}$, and $k_{ex} = k_w + k_1$. When spin-lock pulses are applied on-resonance, $\theta = 90°$ and $\Omega = 0$.

In an on-resonance spin-lock study when $R_{1\rho}$ values are respectively measured at a low achievable SLA $\omega_{1L}$ (eg. 100 Hz), and at a high achievable SLA $\omega_{1H}$ (eg. 400 Hz), the difference $R_{1\rho}$ value can be obtained as:

$$R_{1\rho-Disp} = R_{1\rho}(\omega_{1L}) - R_{1\rho}(\omega_{1H}) = \frac{p \cdot k_{ex} \cdot [(\omega_{1H}/\delta)^2 - (\omega_{1L}/\delta)^2]}{[1 + (\omega_{1H}/\delta)^2] \cdot [1 + (\omega_{1L}/\delta)^2 (k_{ex}/\delta)^2]} \qquad [3]$$

$R_{1\rho-Disp}$ is proportional to $p_1$, the concentration. Since $\omega_{1L}$ and $\omega_{1H}$ can be predetermined and $\delta$ value is fixed, $R_{1\rho-Disp}$ then also depends on $k_{ex}$, which in turn is a function of pH level.

The derivative of Equation 3 with respect to $k_{ex}$ is equal to $$\frac{dR_{1\rho-Disp}}{dk_{ex}} = A \cdot \frac{(k_{ex}^2 - B) \cdot (k_{ex}^2 - C) - 4 \cdot k_{ex}^4}{(k_{ex}^2 + B)^2 \cdot (k_{ex}^2 + C)^2} \qquad [4]$$

where $A = p \cdot \delta^2 (\omega_{1H}^2 - \omega_{1L}^2)$, $B = \delta^2 + \omega_{1H}^2$, $C = \delta^2 + \omega_{1L}^2$. As shown by GAG phantom results (discussed below), in a physiological pH range $A > 0$, $k_{ex}^2 > B$, and $k_{ex}^2 > C$ for —OH protons. Thus $(k_{ex}^2 - B) \cdot (k_{ex}^2 - C) < 4 \cdot k_{ex}^4$ and Equation 4 is always negative, strongly suggesting reduced exchange rate leads to more $R_{1\rho-Disp}$.

RROC

The above discussion shows that both CEST and $R_{1\rho}$ dispersion are roughly proportional to GAG concentration, and are pH level-dependent. Theoretically, $CEST = C \cdot f_1(pH)$ and $R_{1\rho-Disp} C \cdot f_2(pH)$, where C is concentration, and $f_1$ and $f_2$ are functions describing the pH dependence of CEST and $R_{1\rho}$ dispersion, respectively. RROC is defined as the ratio of $R_{1\rho}$ dispersion to CEST:

$$RROC = \frac{f_1(pH)}{f_2(pH)} = f(pH) \qquad [5]$$

where f is a new function describing RROC's pH dependence. When $f_1$ and $f_2$ have different pH responses, RROC is independent of C and yet still dependent of pH as described by f (pH). Therefore it can be used for pH level-dependent imaging.

$R_{1\rho}$ Measurement at Low SLA

Figure 8:
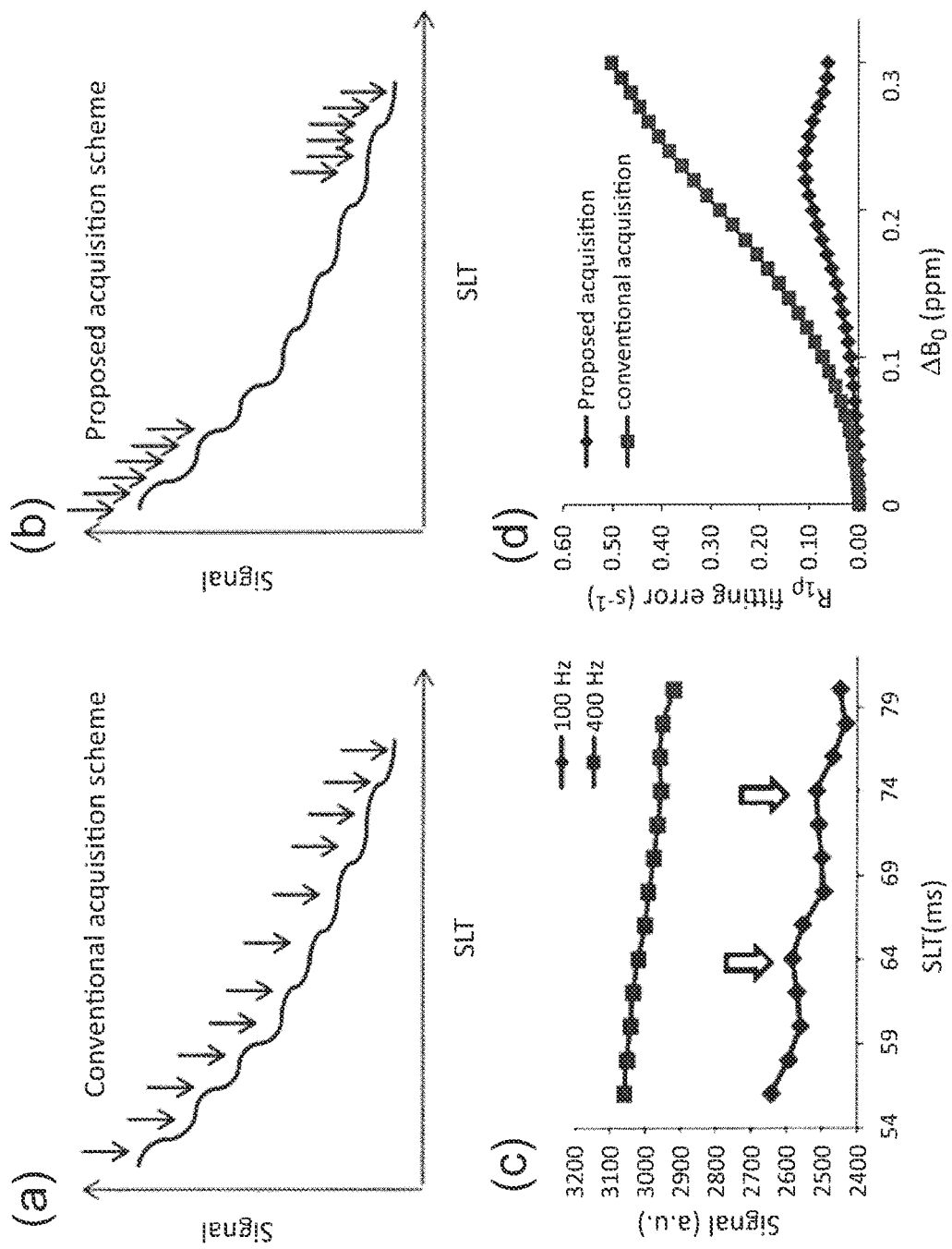
FIG. 8 demonstrates, in accordance with an embodiment of the invention, a spin-lock acquisition scheme under low spin-lock amplitude. a: Conventional acquisition scheme. b: Novel acquisition scheme. c: Spin-lock data of a typical pixel acquired with 100 Hz and 400 Hz amplitude, respectively. Obvious oscillation can be observed in 100 Hz data, whereas 400 Hz data has less oscillation. Arrows point to "peaks" within the oscillation cycle. d: Simulated fitting error of $R_{1\rho}$ under $B_0$ inhomogeneity, for the two acquisitions schemes. The inventive scheme has better immunity to inhomogeneity, and when $\Delta B_0$<0.10 ppm the fitting error is small, indicating the inventive method can compensate $B_0$ inhomogeneity. Simulation is performed with: $R_{1\rho}$=10 s$^{-1}$, $R_{2\rho}$=20 s$^{-1}$, and spin-lock amplitude of 100 Hz.

On-resonance $R_{1\rho}$ measurement is susceptible to $B_0$ and $B_1$ inhomogeneities. Various sequence improvements attempted to address these problems. Among these is a spin-lock preparation called 'phase-cycled composite spin-lock,' which combines phase-cycling and a composite pulse scheme for inhomogeneities compensation (See Chen et al. Quantitative T(1)(rho) imaging using phase cycling for $B_0$ and $B_1$ field inhomogeneity compensation. Magn Reson Imaging 2011:29:608-619, which is incorporated by reference herein in its entirety as though fully set forth). This technique was proven analytically to eliminate $B_1$ inhomogeneity effect. In addition, $B_0$ inhomogeneity effect was also claimed to be corrected, although no analytical proof was provided. Here the analytical description of this technique's dependence on $B_0$ off-resonance (assuming perfect $B_1$) is sought, following the approach used by Li et. al. The magnetization after spin-lock preparation, for odd and even number of acquisitions respectively, can be obtained as:

$$M_{odd} = R_x(\beta) \cdot R_y(\alpha) \cdot (R_x(\theta) \cdot R_z(\partial) E_\rho \cdot R_{-x}(\theta)) \cdot R_y(\alpha) \cdot R_x(\beta) \cdot M(t_0) \quad [6]$$

$$M_{even} = R_{-x}(\beta) \cdot R_y(\alpha) \cdot (R_x(\theta) \cdot R_z(\partial) E_\rho \cdot R_{-x}(\theta)) \cdot R_y(\alpha) \cdot R_x(\beta) \cdot M(t_0) \quad [7]$$

where $M(t_0)$ is the initial magnetization, $R_\varphi(\Phi)$ represents a rotation matrix with flip angle $\Phi$ and orientation $\varphi$, $\beta=90°$ is the flip angle of tip-down/tip-up pulse, $\alpha=135°$, $\theta$ is the angle between effective spin-lock field and z-axis, $$\theta = \tan^{-1}\left(\frac{\omega_1}{\Omega}\right)$$

with $\omega_1$ and $\Omega$ being SLA and frequency offset respectively, $E_\rho$ is a matrix to describe $T_{1\rho}$ and $T_{2\rho}$ (=1/$R_{2\rho}$, the transverse relaxation time in the rotating frame) relaxation, and $\partial$ is the flip angle of spin-lock pulse. The longitudinal magnetization Ai, after phase-cycling is equal to $(M_{even}-M_{odd})/2$, and can be obtained as:

$$M_z = M_0(E_{1\rho} \cdot \sin^2\theta + E_{2\rho} \cdot \cos^2\theta \cdot \cos\xi)$$

where $M_0$ is longitudinal magnetization, $E_{1\rho}=e^{-SLT \cdot R_{1\rho}}$, $E_{2\rho}=e^{-SLT \cdot R_{2\rho}}$, $\xi=2\pi \cdot SLT \cdot \sqrt{(\omega_1)^2+(\Omega)^2}$, and SLT is spin-lock time. When there is $B_0$ off-resonance, the second term in Equation 8 becomes non-zero, causing '$R_{2\rho}$ contamination.' This contamination is dependent on SLA: for a given $\Omega$, a lower $\omega_1$ causes heavier $R_{2\rho}$ contamination. Although it is generally not a problem when imaging with 400 Hz SLA, $R_{1\rho}$ measurement at a low SLA of 100 Hz is complicated by this contamination (FIG. 8 (c)), and correction is needed. The second term in Equation 8 is oscillating at a frequency determined by $\sqrt{(\omega_1)^2+(\Omega)^2}$. For $\omega_1=100$ Hz, this value is much higher than either $R_{1\rho}$ or $R_{2\rho}$ that are on the order of tens of Hz. Thus it is possible to 'filter' the oscillation effects using various data-processing, and obtain only $R_{1\rho}$ related signal.

Here a simple strategy that can easily be applied in a clinical setting is used. Whereas conventional $R_{1\rho}$ measurement includes a number of SLTs that are usually evenly distributed, in the proposed scheme SLTs are divided into two groups with short and long SLTs respectively, and within each group a number of SLTs are used to fully sample at least one cycle of the oscillation. As an example these two types of schemes were compared by numerical simulation: the conventional scheme included 12 SLTs evenly distributed between 10 ms and 150 ms, while the SLTs in the proposed scheme had SLTs of from 10 ms to 20 ms in step of 2 ms, and from 140 ms to 150 ms in step of 2 ms (FIG. 8 (a) & (b)). $R_{1\rho}$ value was obtained by fitting signal to a mono-exponential decay function using least-squares fitting. The absolute errors between fitted $R_{1\rho}$ and the 'true' $R_{1\rho}$ value used in simulation, under different $B_0$ off-resonance, were plotted in FIG. 8 (d). This scheme performed better under $B_0$ off-resonance, especially when $|\Delta B_0|<0.12$ ppm accurate $R_{1\rho}$ quantification can be achieved as the absolute error is close to zero.

Example 9

Methods

Numerical Simulations

Simulations require knowledge of the exchange rate between —OH protons and water protons. An on-resonance spin-lock dispersion study (discussed below) was performed on 9.4T, and $R_{1\rho}$ values were fitted to Equation 2 to obtain exchange rate under different pH levels. Results (Table 2) were subsequently used for simulations. CEST effect on 3.0T was numerically simulated using Bloch-McConnel two-pool exchange model in Matlab (The Mathworks, Natick, Mass.), as described in (Sun, P Z. Simplified and scalable numerical solution for describing multi-pool chemical exchange saturation transfer (CEST) MRI contrast. J. Magn Reson 2010; 205:235-241, which is incorporated herein by reference as though fully set forth). The relaxation and chemical exchange parameters used were chosen to represent typical human IVD: $T_{1w}$=1000 ms, $T_{2w}$=100 ms, $T_{1s}$=500 ms, $T_{2s}$=50 ms. —OH proton offset was 1.0 ppm. GAG concentration was 150 mM assuming 3 —OH protons on each GAG unit. Simulation parameters matched the inventors' in vivo imaging protocol: it included a train of 8 Gaussian pulses of 1440° and a 50% duty cycle, with each pulse lasting 90 ms. The RF pulse profile was extracted from programming platform (IDEA, Siemens AG Healthcare, Erlangen, Germany). It has a normalized average amplitude (p1) of 0.50, and a normalized average power (p2) of 0.38, measured using the metrics previously introduced by Zu et al. (See Optimizing pulsed-chemical exchange saturation transfer imaging sequences. Magn Reson Med 2011; 66:1100-1108, which is incorporated herein by reference in its entirety as though fully set forth). —OH CEST was calculated as the integral of $MTR_{asym}$ between 0.5 ppm and 1.5 ppm. $R_{1\rho}$ dispersion between SLAs of 100 Hz and 400 Hz was simulated based on Equation 3. RROC was calculated subsequently.

TABLE 2

Fitted Results under Different pH Levels

| | pH | | | |
|---|---|---|---|---|
| | 6.00 | 6.40 | 6.68 | 7.04 |
| Exchange rate $k_{ex\,(s^{-1})}$ | 504 | 646 | 749 | 834 |
| Concentration ρ1 | 0.011 | 0.012 | 0.016 | 0.015 |
| Transverse relaxation rate $R_2$ ($s^{-1}$) | 1.71 | 1.76 | 1.65 | 1.72 |

Phantoms

Phantom I: To quantify the exchange rate of GAG phantoms under different pH levels at 9.4T, GAG samples with a concentration of 150 mM were prepared from chondroitin sulphate A (Aldrich-Sigma, St. Louis, Mo., USA) in a standard solution of phosphate-buffered saline, and their pH levels were subsequently titrated to 7.04, 6.68, 6.40, and 6.00 respectively. The concentration refers to the number of disaccharide units in GAGs. Phantom II: To verify the dependence of CEST and $R_{1\rho}$ dispersion on GAG concentration and pH at 3.0T, in a different study 4 samples of GAGs with concentrations of 50, 100, 150 and 200 mM respectively were prepared from chondroitin sulphate A in a standard solution of phosphate-buffered saline. Then each sample was divided evenly into five smaller tubes, and their pH levels were titrated to values around 7.2, 7.0, 6.7, 6.3 and 6.0 respectively. At time of imaging the samples were placed in gadolinium-doped water bath.

Porcine Spine

Porcine spine thoracolumbar was harvested from a freshly sacrificed Yucatan minipig. Sample was immediately taken to a −20° C. freezer for storage and taken to room temperature at least 24 hours before MRI to defrost. After removal of the surrounding muscles and posterior elements, a small cut (~3 mm) was made at the middle of each intervertebral disc parallel to the endplates using a scalpel. 0.05 mL Na-Lactate (Sodium L-Lactate, Sigma Aldrich, St. Louis, Mo.) with different concentrations was injected into nucleus pulposus in order to induce a variety of pH levels within the discs. pH was measured using a custom-made tissue pH probe (Warner Instruments, LLC, Hamden, Conn.) by inserting the electrode into the center of the disc.

Human Subjects

Four male (ages 42.8±18.3) and two female (ages 55.5±2.1) subjects with chronic low back pain (>6 months) due to moderate degenerative disc disease at any lumbar level and scheduled for provocative discography were recruited. Inclusion criteria were: failure of conservative therapy for at least 3 months (including physical therapy), low back pain of at least 40 mm on a 100 mm Visual Analog Scale with either leg pain less than back pain or nonradicular of origin, lumbar disc pathology having a modified Pfirrmann score of 3, 4, 5 or 6, with a herniation of no greater than 6 mm and no neurological compression, and pain/pathology not originated from facet joints or stenosis. Outcomes of discography were classified as either positive or negative. A total of 23 disc levels were studied. MRIs were performed 1-4 (average=1.9) weeks before scheduled discography to avoid compounding effects of potential disc damage caused by the procedure.

MRI Acquisitions

Phantom I was scanned on a 9.4 T Bruker Biospec Imager (Bruker Biospin, Billerica, Mass., USA), using a volume transmit and receive RF coil. Image readout was single-slice rapid acquisition with refocused echoes (RARE) sequence with spin-lock preparation. SLAs were from 298 Hz to 1746 Hz in step of 85 Hz. SLTs were 50, 100, 150, and 200 ms. Phantom II and porcine spine were performed on a 3.0T clinical scanner (Magnetom Verio, Siemens AG Healthcare, Erlangen, Germany). RF was transmitted using body coil. CEST and water saturation shift referencing (WASSR) preparation were similar to the inventors' study described in Experiments I (above). Shimming was done manually. Spin-lock preparation was achieved by using phase-cycling preparation and the new acquisition scheme. SLAs were 100 and 400 Hz. SLTs were from 22 ms to 40 ms in step of 2 ms, and from 122 ms to 140 ms in step of 2 ms. Imaging of Phantom II in the axial plane was conducted using CEST and spin-lock turbo-spin-echo (TSE), with a 24-elements spine coil and a body matrix coil. Three IVDs of the porcine spine were individually scanned with a 2D axial slice, using CEST and spin-lock TSE.

A two-dimension (2D) reduced field-of-view (rFOV) TSE CEST sequence was previously introduced, as discussed above. As indicated above, rFOV can effectively suppress motion artifacts caused by bowel movement, and improve measurement reproducibility. This is important for quantitative IVD imaging which is susceptible to artifacts. The same rFOV TSE pulse sequence design was applied to spin-lock preparation, forming an rFOV TSE spin-lock sequence for human imaging at 3.0T. Following localizer and standard $T_1/T_2$-weighted TSE acquisitions, on each patient a 2D sagittal slice cutting through the center of IVDs was used for CEST and spin-lock imaging. Only the spine coil was used for signal receiving. The WASSR offset frequency range was sufficient to cover maximum frequency shift after careful shimming with the shim box selected to only cover interested spine region. The WASSR saturation power was enough to achieve water resonance frequency quantification. Imaging parameters are shown in Table 3. CEST and WASSR preparation parameters are shown in Table 4. For spin-lock preparation, SLAs were 100 and 400 Hz. SLTs were from 22 ms to 40 ms in step of 2 ms, and from 102 ms to 120 ms in step of 2 ms.

TABLE 3

3.0T Human Imaging Parameters

| Sequence | TE (ms) | TR (ms) | TH (mm) | FOV (mm²) | ETL | Matrix | No. of Avgs. | TA (min) |
|---|---|---|---|---|---|---|---|---|
| rFOV CEST | 9 | 3000 | 8 | 73 × 220 | 42 | 32 × 192 (interpolated to 64 × 384) | 4 | 5.4 |
| rFOV Spin-lock | 9 | 3000/5830-8050[a] | 8 | 73 × 220 | 42 | 32 × 192 (interpolated to 64 × 384) | 4 | 11.8-18.5 |

[a]TR was fixed at 3000 ms for 100 Hz scan. The minimum allowable TR was used for 400 Hz scan.
TE = echo time;
TR = repetition time;
TH = slice thickness;
rFOV = reduced field-of-view;
ETL = echo train length;
TA = imaging time

TABLE 4

3.0T Human CEST Parameters

| Sequence | FA (°) | RF duration (ms) | No. of RFs | No. of offsets | Offset range (ppm) | Irradiation time (ms) | Irradiation power (μT) |
|---|---|---|---|---|---|---|---|
| CEST | 1440 | 90 | 8 | 15 | −2.1 to 2.1 | 1350 | 0.9 |
| WASSR | 60 | 30 | 2 | 11 | −1.0 to 1.0 | 90 | 0.09 |

Data Analysis

Post processing was performed with custom-written programs in Matlab (The Mathworks, Natick, Mass.). CEST images were processed as described in Experiments I (above). Spin-lock images at different SLTs were fitted into a mono-exponential decay model to obtain $R_{1\rho}$ values using least-squares fitting, pixel by pixel. On phantom images user-defined region-of-interest (ROI) containing at least 100 pixels inside GAG regions was drawn manually. For porcine and human IVD data, ROI was chosen to only include central NP region that has high signal on MRI, due to concerns of insufficient SNR in outer NP and AF regions. When drawing ROI on porcine IVDs, regions with NP leakage as a result of opened disc were carefully avoided. CEST and $R_{1\rho}$ dispersion values were averaged within ROI before RROC calculation. In addition, normalized RROC for each human IVD was calculated by dividing the corresponding RROC value by the lowest value in each subject. This normalization could help to reduce variations among subjects. Two discs from patient #2 were excluded from subsequent analysis because of negative $R_{1\rho}$ dispersion values, which were possibly caused by small $R_{1\rho}$ dispersion, noises due to limited SNR, and poor shimming. A total of 21 human discs were analyzed.

Statistics

Statistical analysis was performed using SPSS v. 16.0 (SPSS, Chicago, Ill.). Paired-t test was used to test RROC value differences between IVDs with positive and negative discography outcomes with the significant level defined at $\alpha=0.05$. Receiver-operating characteristic (ROC) curves were generated for RROC as disc pain biomarker and areas under the curve (AUC) were calculated.

Example 10

Results

Fitted exchange rate $k_{ex}$ of the —OH protons under different pH levels are shown in Table 2. These rates are in the intermediate exchange regime and lower pH leads to reduction in exchange rate, meaning —OH exchange is mainly base-catalyzed, similar to measurements of amine protons (27). When $\omega_{1H}$=400 Hz and $\omega_{1L}$=100 Hz, B and C as defined in Equation 4 are $1.8\times10^5$ and $2.6\times10^4$ respectively, which are smaller than the lowest $k_{ex}^2$ of $4.1\times10^5$. This indicates for pH levels in the physiological range, Equation 4 is negative and thus a lower pH level will lead to more $R_{1\rho}$ dispersion in GAGs. However, when $\omega_{1H}$ becomes too large then this statement will be violated, and the monotone decreasing relation between $R_{1\rho}$ dispersion and pH may no longer hold.

Figure 9:
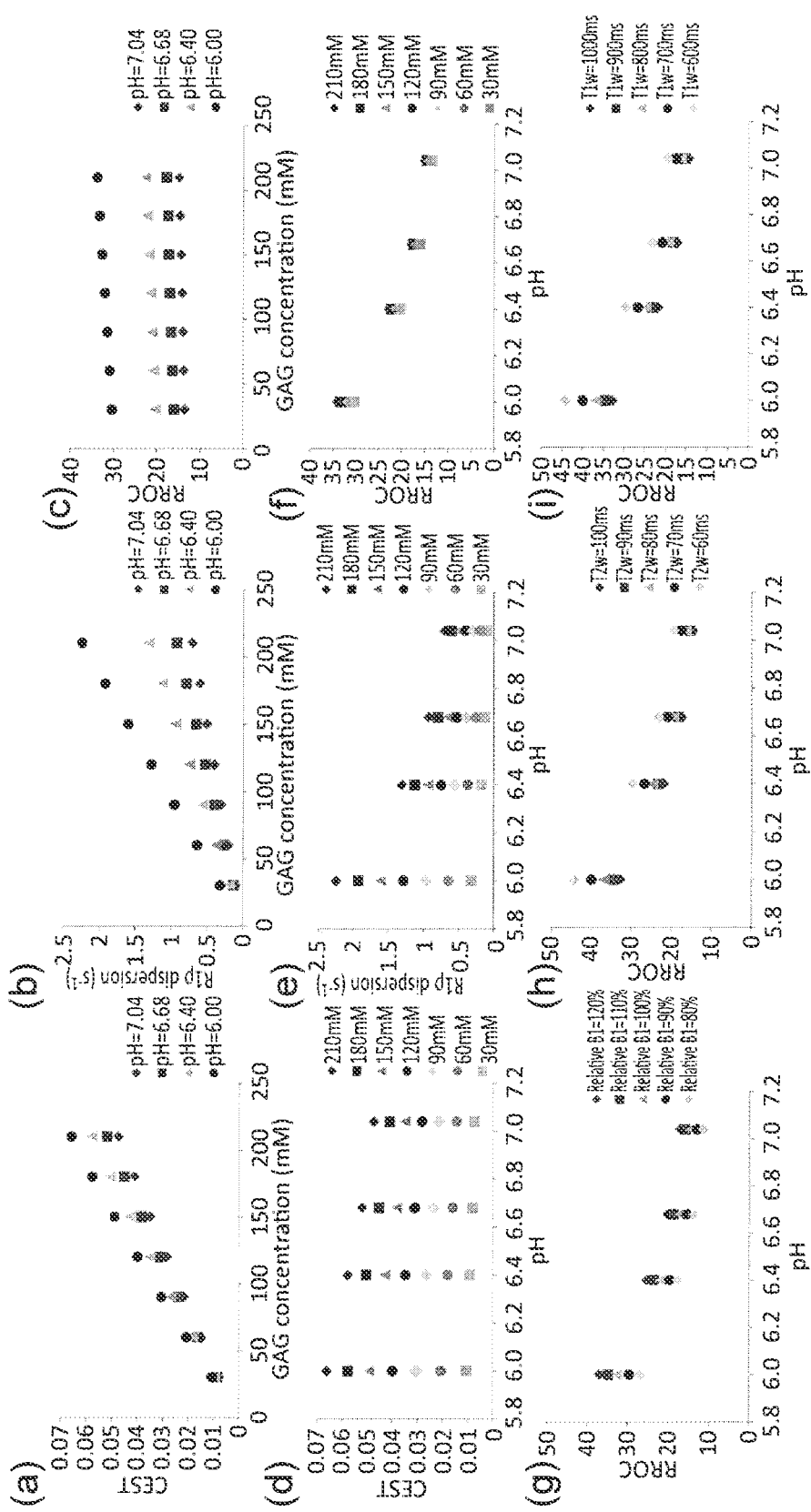
FIG. 9 demonstrates, in accordance with an embodiment of the invention, simulated GAG CEST, $R_{1\rho}$ dispersion, and RROC with respect to GAG concentration (ac) and to pH (d-f), and dependence of RROC on $B_1$ error (g), $T_{2w}$ (h), and $T_{1w}$(i). RROC is almost insensitive to changes in concentration, because the division of $R_{1\rho}$ dispersion and CEST has cancelled the concentration effect but maintains its dependence on pH. RROC is moderately affected by changes in relative $B_1$, $T_{2w}$, and $T_{1w}$.

Simulation results are shown in FIG. 9. Both CEST and $R_{1\rho}$ dispersion were proportional to concentration as shown in FIG. 9a and FIG. 9b. Compared with CEST, $R_{1\rho}$ dispersion was more sensitive to pH changes as reflected by a larger slope in FIG. 9e compared with in FIG. 9d. RROC was almost independent of concentration and dependent on pH as shown in FIG. 9c and FIG. 9f. Simulation indicates that RROC can serve as a concentration independent, pH level-dependent imaging biomarker.

Figure 10:
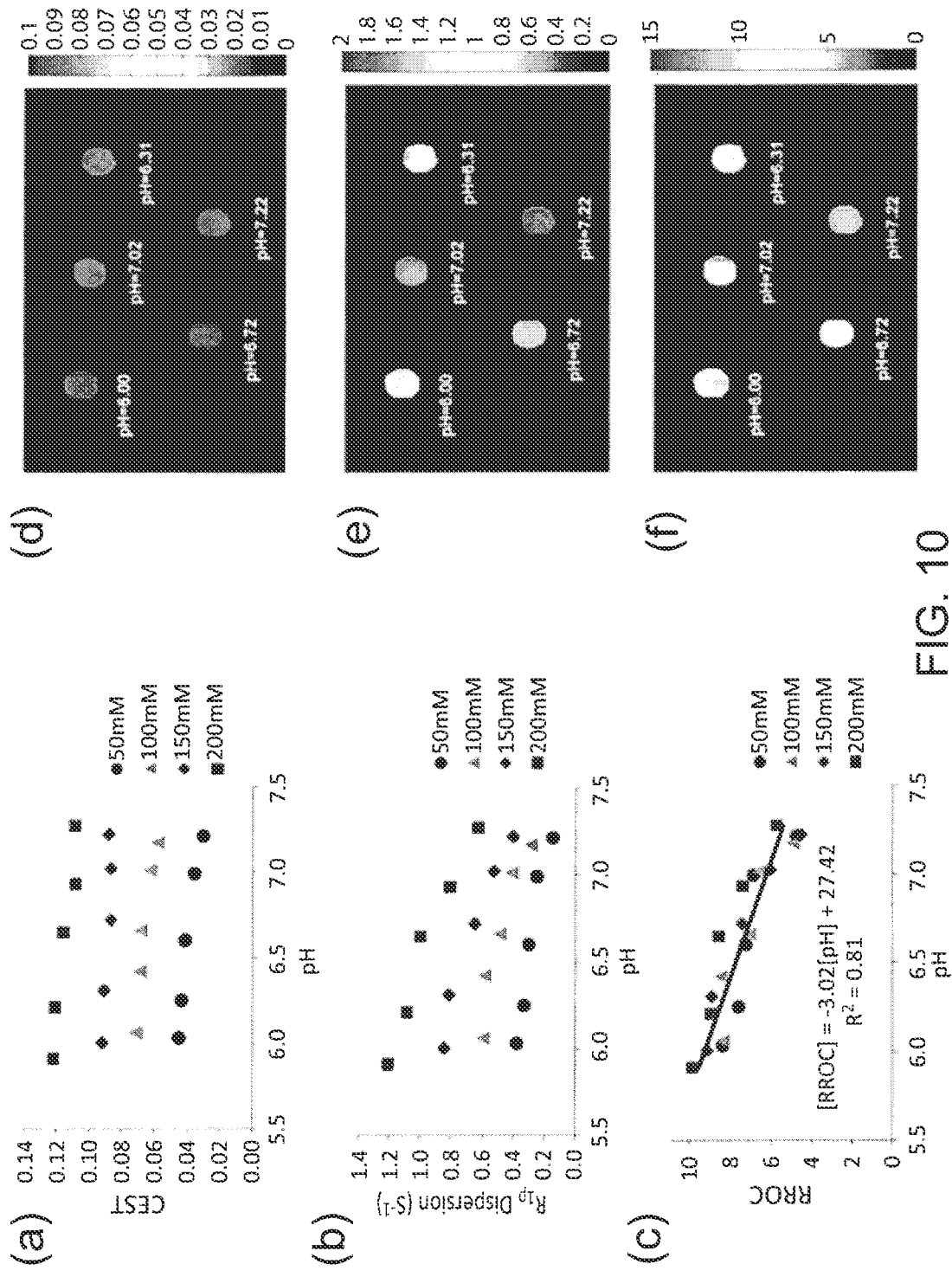
FIG. 10 demonstrates, in accordance with an embodiment of the invention, GAG phantoms results on 3.0T. a-c: Show the pH dependence of CEST, $R_{1\rho}$ dispersion, and RROC of phantoms with various concentrations, respectively. d-f: Show CEST, $R_{1\rho}$ dispersion, and RROC images for the 150 mM GAGs.

Phantom II results are shown in FIG. 10. While both CEST and $R_{1\rho}$ dispersion were dependent on pH, $R_{1\rho}$ dispersion was more sensitive to changes in pH level, as seen by the larger slope in FIG. 10b compared with in FIG. 10a. Results shown in FIG. 10c confirmed the concentration independence and pH level dependence of RROC. CEST, $R_{1\rho}$ dispersion, and RROC images FIGS. 10d-f of the 150 mM phantoms demonstrated the pH level-dependent imaging capability of the proposed technique, as GAGs with different pH levels were well discriminated in FIG. 10f. It is worth mentioning that Phantom II and simulation RROC results differ in values, because simulations were performed with parameters that of typical in vivo IVD rather than GAGs. Nevertheless similar pH dependence trends were observed in both studies, supporting that RROC is suitable for pH level-dependent imaging.

Figure 11:
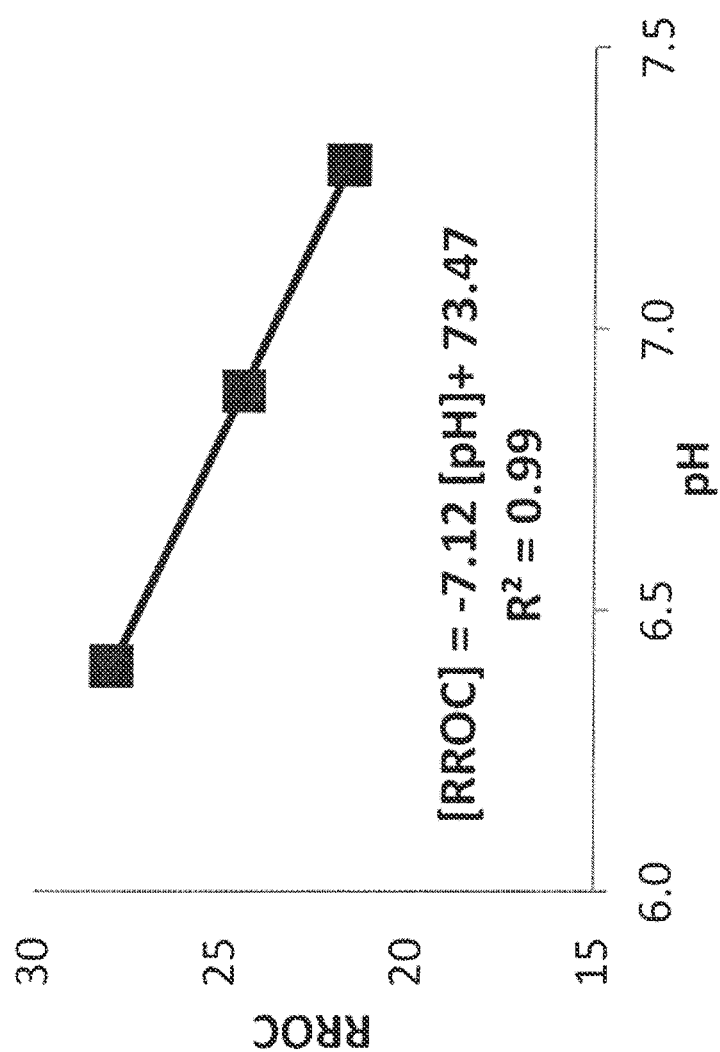
FIG. 11 demonstrates, in accordance with an embodiment of the invention, results of three porcine IVDs following Na-Lactate injection to manipulate pH level. A negative correlation was observed between RROC and pH.

The ability of pH level-dependent imaging was tested on porcine spine IVDs, with results shown in FIG. 11. Of the 3 discs studied, a reduced pH was correlated with higher RROC. These RROC values differ from that of GAG phantoms because they had different MR parameters such as T1 and T2. Nevertheless a similar pH dependence trend was observed.

Figure 12:
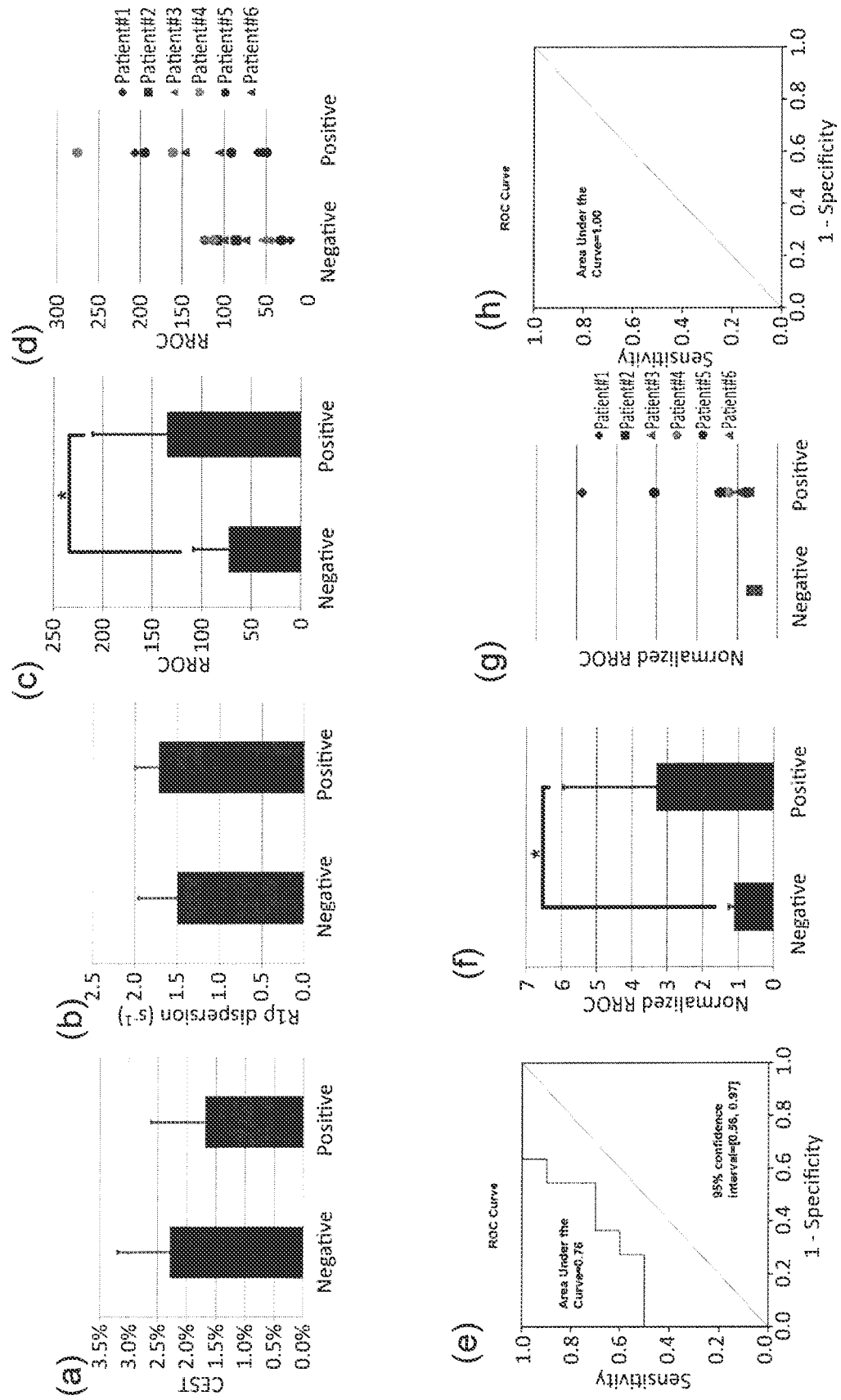
FIG. 12 demonstrates, in accordance with an embodiment of the invention, patient results. a,b: —OH CEST and $R_{1\rho}$ dispersion values for positive and negative discs, respectively. c,f: the difference in RROC and normalized RROC between positive and negative discs, respectively. d,g: RROC and normalized RROC of individual discs, respectively. e,h: ROC curves for RROC and normalized RROC, respectively. Stars indicate significant difference by paired t-test (P<0.05).

Patient results are shown in FIG. 12. The average RROC values of painful and non-painful discs based on discography were 135±75 and 73±36, respectively (mean±SE), and significant difference was identified between them by paired t-test (P=0.024). The higher RROC values in painful discs suggested a lower pH level. This finding was in line with predictions from LBP pathogenesis theories and studies. ROC analysis had an AUC of 0.76, indicating it is a fair predictor for painful discs. To correct for variations between human subjects, RROC values were then normalized by the smallest value in each subject. The average normalized RROC values of painful and non-painful discs based on discography were 3.3±2.6 and 1.1±0.2, respectively (mean±SE), and significant difference was identified between them by paired t-test (P=0.013). ROC analysis revealed that this approach has high prediction power with an AUC of 1.00.

Normalization Improved the Technique's Predictability.

Figure 13:
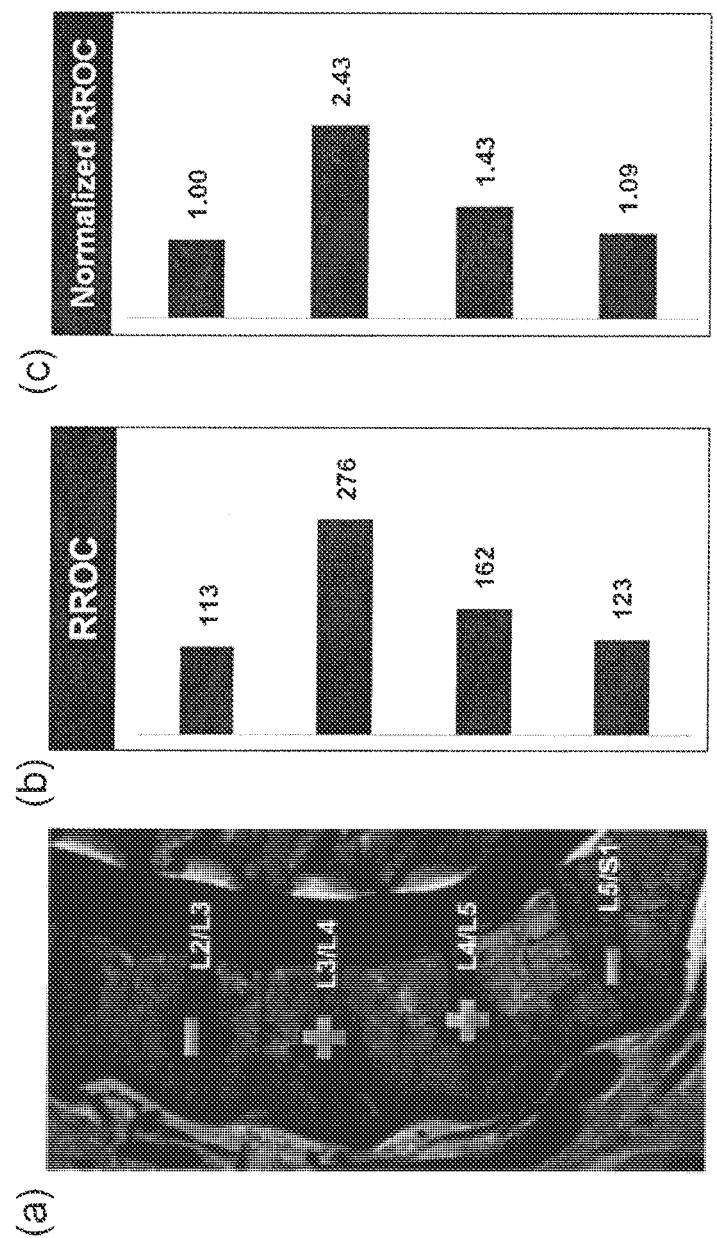
FIG. 13 demonstrates, in accordance with an embodiment of the invention, a typical patient result (62Y/M). A $T_{2w}$ TSE image with discography outcome ("+" and "−" for positive and negative, respectively) (a), RROC (b), and normalized RROC (c) values, respectively, for the four discs labeled.

Imaging results of a typical patient are shown in FIG. 13. In this subject 2 positive and 2 negative discs were identified by discography FIG. 13a. Thresholds can be drawn between painful and non-painful discs, both in RROC and normalized RROC results FIG. 13b-c.

Example 11

Discussion

In some embodiments, the invention teaches a novel pH level-dependent imaging technique. This technique does not depend on exogenous contrast agents, and can be applied on a 3.0T scanner. A concentration independent and pH level-dependent new index, RROC, was proposed as a suitable biomarker for pH imaging in the IVDs. A negative correlation between RROC and pH levels was discovered by numerical simulations, phantoms and porcine spine studies, in a physiological pH range. The patient study showed significantly higher RROC values in painful IVDs, and normalized RROC demonstrated great power in predicting painful discs. These results suggest that 1) painful discs are associated with lower pH levels, and 2) the proposed technique is a promising, non-invasive method for detecting discogenic low back pain.

The relation between —OH CEST and pH demonstrated herein is different from that reported by Melkus et al. (See Melkus et al. Ex vivo porcine model to measure pH dependence of chemical exchange saturation transfer effect of glycosaminoglycan in the intervertebral disc. Magn Reson Med 2013. Doi: 10.1002/mrm.24838, which is incorporated herein by reference in its entirety as though fully set forth), where complicated pH level-dependence was observed when a large pH range was investigated. When focusing on the physiological pH range of 7.2 to 6.0, —OH CEST in the study reported herein increased with decreased pH level, whereas the opposite trend was observed in their study. The discrepancies could be attributed to different magnetic fields, effect of DS, and saturation pulse profile. Specifically, their study was performed at 7.0 Tesla, which has a higher resonance frequency. An exchange rate of 600 Hz may be considered to fall within intermediate exchange regime at 3.0 T, at 7.0 T it may be closer to slow exchange regime, and thus a different pH dependence relationship should be expected. Another important factor is DS of water pool as a result of non-negligible saturation pulse bandwidth. This is especially relevant for —OH imaging as their resonance frequencies are close to water (~125 Hz on 3.0T and 292 Hz on 7.0T). At higher magnetic field since —OH protons are more separated from water peak generally less direct saturation effect is expected. Saturation pulse profile does matter as well. It has been previously shown that pulse shape has influences on gagCEST. The use of normalized average amplitude (p1) and normalized average power (p2) as metrics to describe pulsed-CEST has also been proposed. Even though those studies used Gaussian pulses, pulse profile differences (eg. p1 and p2) could lead to different CEST signal. Therefore the dependence of —OH CEST on pH has to be characterized on each platform carefully.

The two-pool $R_{1\rho}$ dispersion model as shown in Equation 2 only involves —OH and water protons, and neglects —NH protons. Jin et al. concluded that on-resonance spin-lock is most sensitive to intermediate exchange regime. GAG —OH has an exchange rate between 640 Hz and 930 Hz as measured in the inventors' experiment. The exact GAG —NH exchange rate is unknown. In the brain —NH exchange rate has been measured to be ~10-30 Hz. Previous ex vivo results revealed that GAG —NH CEST signal is roughly one order smaller than —OH, indicating GAG —NH is likely to exchange with a slow rate as well. Therefore in this case the two-pool $R_{1\rho}$ chemical exchange model should be sufficient. In cases where there are multiple exchanging protons each having substantial contribution, a multi-pool model should be considered. In these cases contribution to $R_{1\rho}$ from chemical exchange is the sum of contributions of each of the proton pools. For protons with $k_{ex}^2 > B$, Equation 4 is negative, meaning a reduced $k_{ex}$ will lead to increased $R_{1\rho}$ dispersion. For those with $C < k_{ex}^2 < B$, Equation 4 is still negative. Only when $k_{ex}^2 < C$, or $k_{ex} < 161$ Hz, a non-monotonic relationship exist between $R_{1\rho}$ dispersion and pH. However this already falls into slow exchange regime, and its contribution to chemical exchange is limited. Therefore for most metabolites that have substantial $R_{1\rho}$ dispersion, a reduced $k_{ex}$ will lead to larger $R_{1\rho}$ dispersion. Furthermore, considering commonly seen exchangeable protons in the intermediate exchange regime such as amine and —OH are base-catalyzed within physiological pH range, a decrease in pH level will typically lead to larger $R_{1\rho}$ dispersion, on a 3.0T clinical scanner using similar parameters as in our study.

Some confounding factors remain that could complicate pH-level dependent imaging with the inventive RROC technique. The first type of confounders include MR parameters such as T1 and T2. Although no mathematical description is available for pulsed-CEST imaging, for continuous-pulse imaging T1 and T2 do contribute to CEST signal as revealed by analytical solutions discussed previously. Therefore it is possible that such MR parameters could confound pH level-dependent imaging by affecting CEST signal, and may require further correction. In fact when RROC values were normalized by subject in the patient study, the AUC value in ROC test increased from 0.76 to 1.00, indicating the normalization process brought more prediction power in identifying painful discs, possibly by reducing variations in T1 and T2 between subjects but not within subject. Another potential approach is to first examine the relationship between RROC and T1 and T2 using numerical simulations and phantom studies, then perform T1 and T2 quantification during MRI acquisition, and finally correct the measured RROC value using T1 and T2 values. However this approach comes at a cost of prolonged imaging time. The second type of confounders includes alternative saturation transfer mechanisms including conventional MT and nuclear Overhauser effect (NOE). Underlying MT effects stem from semi-solid components such as macromolecules, and always accompany CEST in tissues. MT is asymmetric and cannot be corrected by $MTR_{asym}$ analysis. NOEs on GAG were identified at −2.6 ppm and −1.0 ppm. These negative NOEs lowers measured CEST signal. Although in healthy IVDs the high —OH CEST as a result of high GAG concentration may override the NOE at −1.0 ppm, in severely degenerated IVDs this may not be true.

It is worth noting that certain parameters were not experimentally optimized. For example, the amplitudes of 100 Hz and 400 Hz used for $R_{1\rho}$ dispersion measurement were chosen empirically. The 400 Hz was chosen because it permits pulse sequence execution on all subjects without encountering any problem with specific absorption rate (SAR) or RF amplifier. A higher $\omega_{1H}$ should be used whenever possible, because a larger dispersion allows more accurate measurement. The 100 Hz was chosen because sometimes artifacts were found at a SLA lower than 100 Hz in the inventors' experiment. Alternatively instead of 100 Hz spin-lock one would think of using T2 quantification, which provides a larger dispersion. T2 quantification may require a separate preparation as compared to spin-lock, as recently demonstrated by Li et al. (See Li et al. Simultaneous acquisition of T1ρ and T2 quantification in knee cartilage: repeatability and diurnal variation Magn Reson Imaging 2013. Doi: 10.1002/jmri.24253, which is incorporated herein by reference in its entirety as though fully set forth). Care has to be taken interpreting dispersion data measured using two different preparation schemes. Nevertheless, optimization involving numerical simulations, phantom study and in vivo study is recommended.

Example 12

Conclusion

In certain embodiments, the invention teaches a pH level-dependent, concentration independent index RROC for pH imaging in the IVDs, by combining $R_{1\rho}$ dispersion and CEST imaging. To facilitate measuring this new index on a 3.0T scanner, rFOV technique and a novel spin-lock acquisition scheme under low spin-lock amplitude were used. Studies demonstrated a negative correlation between RROC values and pH levels. Normalized RROC successfully detected all painful discs in the preliminary patient study. As a non-invasive, pH level-dependent imaging tool, this technique could be used to 1) diagnose painful discs, 2) contribute to the understanding of LBP pathogenesis, and 3) provide insights on development of novel therapeutic approaches.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for diagnosing a subject with the presence or absence of a condition characterized by tissue degeneration and/or pain, comprising:
    performing a scan of a region of the subject's body using a magnetic resonance imaging (MRI) scanner;
    generating an image of the region of the subject's body from the performed scan using Reduced-Field-of-View Turbo-Spin-Echo Chemical Exchange Saturation Transfer (rFOV TSE CEST) imaging,
        wherein the Reduced-Field-of-View Turbo-Spin-Echo Chemical Exchange Saturation Transfer (rFOV TSE CEST) imaging comprises moving gradients of 180° refocusing pulses from a slice-encoding direction to a phase-encoding direction to obtain a reduced field of view;
    processing the image to detect one or more biomarkers within the image of the region,
        wherein the biomarkers are selected from the group consisting of pH, glycosaminoglycan (GAG) concentration, glucose concentration, and lactate concentration; and
    diagnosing the subject with the presence or absence of the condition based upon the biomarkers detected within the image of the region of the subject's body.

2. The method of claim 1, wherein the image of the region of the subject's body comprises a joint or an intervertebral disc.

3. The method of claim 1, wherein the condition is selected from the group consisting of: intervertebral disc degeneration, discogenic pain, osteoarthritis, rheumatoid arthritis, an articular cartilage injury, tempromandibular disc degeneration and combinations thereof.

4. The method of claim 1, wherein the biomarkers are selected from pH and glycosaminoglycan (GAG) concentration.

5. The method of claim 1, wherein the subject is diagnosed with the condition if the biomarkers detected from scanning indicate one or more abnormal physiological states within the image of the region compared to a subject without the condition.

6. The method of claim 5, further comprising determining that an origin of the subject's pain associated with the condition is within the region of the subject's body where the abnormal physiological state is detected.

7. The method of claim 1, wherein a slice thickness for the MRI scan is selected so as to avoid fat signal interference.

8. The method of claim 7, wherein the slice thickness is 3 mm.

9. The method of claim 1, wherein the MRI scanner is a 3.0T MRI scanner.

10. The method of claim 1, wherein the image is a CEST image.

11. A method for prognosing a condition associated with tissue degeneration and/or pain in a subject, comprising:
performing a scan of a region of the subject's body using a magnetic resonance imaging (MRI) scanner;
generating an image of the region of the subject's body from the performed scan using Reduced-Field-of-View Turbo-Spin-Echo Chemical Exchange Saturation Transfer (rFOV TSE CEST) imaging,
wherein the Reduced-Field-of-View Turbo-Spin-Echo Chemical Exchange Saturation Transfer (rFOV TSE CEST) imaging comprises moving gradients of 180° refocusing pulses from a slice-encoding direction to a phase-encoding direction to obtain a reduced field of view;
processing the image to detect one or more biomarkers within the image of the region,
wherein the biomarkers are selected from the group consisting of pH, glycosaminoglycan (GAG) concentration, glucose concentration, and lactate concentration; and
prognosing the condition by comparing measurements of one or more biomarkers detected within the image of the region to previous measurements of the same one or more biomarkers detected within the image of the region.

12. The method of claim 11, wherein the condition is selected from the group consisting of: intervertebral disc degeneration, discogenic pain, osteoarthritis, rheumatoid arthritis, an articular cartilage injury, tempromandibular disc degeneration and combinations thereof.

13. The method of claim 11, wherein the image of the region of the subject's body comprises a joint or an intervertebral disc.

14. The method of claim 11, wherein the biomarkers are selected from pH and glycosaminoglycan (GAG) concentration.

15. The method of claim 11, wherein a slice thickness for the MRI scan is selected so as to avoid fat signal interference.

16. The method of claim 15, wherein the slice thickness is 3 mm.

17. The method of claim 11, wherein the image is a CEST image.

18. A method for determining an extent of intervertebral disc (IVD) degeneration in a subject, comprising:
performing a scan of a region of interest in the subject using a magnetic resonance imaging (MRI) scanner,
generating an image of the region of interest from the performed scan using Reduced-Field-of-View Turbo-Spin-Echo Chemical Exchange Saturation Transfer (rFOV TSE CEST) imaging,
wherein the Reduced-Field-of-View Turbo-Spin-Echo Chemical Exchange Saturation Transfer (rFOV TSE CEST) imaging comprises moving gradients of 180° refocusing pulses from a slice-encoding direction to a phase-encoding direction to obtain a reduced field of view, and
wherein the region of interest comprises an intervertebral disc;
obtaining an —OH chemical exchange saturation transfer (—OH CEST) signal from the MRI scan; and
determining the extent of IVD degeneration in the subject, wherein a lower —OH CEST signal, compared to normal, indicates disc degeneration, and wherein the lower the —OH CEST signal is, the greater the extent of IVD degeneration determined.

19. The method of claim 18, wherein a slice thickness for the MRI scan is selected so as to avoid fat signal interference.

20. The method of claim 19, wherein the slice thickness is 3 mm.

21. A method for identifying a painful intervertebral disc (IVD) in a subject, comprising:
performing a scan of a region of interest in the subject using a magnetic resonance imaging (MRI) scanner;
generating an image of the region of interest from the performed scan using Reduced-Field-of-View Turbo-Spin-Echo Chemical Exchange Saturation Transfer (rFOV TSE CEST) imaging,
wherein the Reduced-Field-of-View Turbo-Spin-Echo Chemical Exchange Saturation Transfer (rFOV TSE CEST) imaging comprises moving gradients of 180° refocusing pulses from a slice-encoding direction to a phase-encoding direction to obtain a reduced field of view, and
wherein the region of interest comprises an intervertebral disc;
determining $R_{1\rho}$ dispersion and —OH CEST in the region of interest; and
identifying a painful IVD in the subject based upon the ratio of $R_{1\rho}$ dispersion and —OH CEST (RROC), wherein a painful disc is determined if an RROC value is high compared to normal.

22. The method of claim 21, wherein the MRI scanner is a 3.0T MRI scanner.

23. The method of claim 21, wherein a slice thickness for the MRI scan is selected so as to avoid fat signal interference.

24. The method of claim 23, wherein the slice thickness is 3 mm.

25. A method for determining an extent of intervertebral disc (IVD) regeneration in a subject, comprising:
performing a scan of a region of interest in the subject using a magnetic resonance imaging (MRI) scanner,
generating an image of the region of interest from the performed scan using Reduced-Field-of-View Turbo-Spin-Echo Chemical Exchange Saturation Transfer (rFOV TSE CEST) imaging,
wherein the Reduced-Field-of-View Turbo-Spin-Echo Chemical Exchange Saturation Transfer (rFOV TSE CEST) imaging comprises moving gradients of 180° refocusing pulses from a slice-encoding direction to a phase-encoding direction to obtain a reduced field of view, and
wherein the region of interest comprises an intervertebral disc;
obtaining an —OH chemical exchange saturation transfer (—OH CEST) signal from the MRI scan; and
determining the extent of IVD regeneration in the subject, wherein a higher —OH CEST signal, compared to normal, indicates disc regeneration, and wherein the higher the —OH CEST signal is, the greater the extent of IVD regeneration determined.

26. The method of claim 25, wherein a slice thickness for the MRI scan is selected so as to avoid fat signal interference.

27. The method of claim 26, wherein the slice thickness is 3 mm.

* * * * *